United States Patent
Labaudiniere

(10) Patent No.: US 7,868,033 B2
(45) Date of Patent: Jan. 11, 2011

(54) COMPOUNDS, COMPOSITIONS AND METHODS FOR STABILIZING TRANSTHYRETIN AND INHIBITING TRANSTHYRETIN MISFOLDING

(75) Inventor: Richard Labaudiniere, Sherborn, MA (US)

(73) Assignee: FoldRx Pharmaceuticals, Inc., Cambridge, MA (US)

( * ) Notice: Subject to any disclaimer, the term of this patent is extended or adjusted under 35 U.S.C. 154(b) by 284 days.

(21) Appl. No.: 11/134,628

(22) Filed: May 20, 2005

(65) Prior Publication Data

US 2005/0282780 A1 Dec. 22, 2005

Related U.S. Application Data

(60) Provisional application No. 60/573,720, filed on May 20, 2004.

(51) Int. Cl.
*A61K 31/423* (2006.01)
*C07D 263/57* (2006.01)
(52) U.S. Cl. .................. 514/375; 548/224; 548/110
(58) Field of Classification Search ................ 548/110, 548/224; 514/375
See application file for complete search history.

(56) References Cited

U.S. PATENT DOCUMENTS

| 3,551,443 | A | 12/1970 | Duennenberger et al. |
| RE29,608 | E | 4/1978 | Evans et al. |
| 4,107,169 | A | 8/1978 | Schrage |
| 4,416,892 | A | 11/1983 | Dawson |
| 5,037,842 | A | 8/1991 | Goldstein |
| 5,200,420 | A | 4/1993 | Goldmann et al. |
| 5,254,692 | A | 10/1993 | Goldmann et al. |
| 5,354,759 | A | 10/1994 | Oku et al. |
| 5,412,099 | A | 5/1995 | Goldmann et al. |
| 5,441,946 | A | 8/1995 | Pauls et al. |
| 5,552,426 | A | 9/1996 | Lunn et al. |
| 5,563,128 | A | 10/1996 | Pauls et al. |
| 5,714,496 | A | 2/1998 | Brown et al. |
| 5,837,390 | A | 11/1998 | Kishii et al. |
| 6,107,491 | A | 8/2000 | Eldin |
| 6,277,853 | B1 | 8/2001 | Perez et al. |
| 6,420,418 | B1 | 7/2002 | Hagmann et al. |
| 6,495,568 | B1 | 12/2002 | Dack et al. |
| 6,544,989 | B2 | 4/2003 | Mathews et al. |
| 6,589,953 | B2 | 7/2003 | Perez et al. |
| 6,602,619 | B2 | 8/2003 | Lin et al. |
| 6,623,930 | B2 | 9/2003 | Kerwin et al. |
| 6,689,887 | B2 | 2/2004 | Kerwin et al. |
| 6,693,098 | B2 | 2/2004 | Cournoyer et al. |
| 6,794,403 | B2 | 9/2004 | Malamas et al. |
| 2001/0056100 | A1 | 12/2001 | Cournoyer et al. |
| 2002/2049142 | | 4/2002 | Mathews et al. |
| 2002/2061891 | | 5/2002 | Perez et al. |
| 2002/2107258 | | 8/2002 | Kerwin et al. |
| 2003/0040525 | A1 | 2/2003 | Kerwin et al. |
| 2003/0129448 | A1 | 7/2003 | Lin et al. |
| 2003/0199562 | A1 | 10/2003 | Malamas et al. |
| 2003/0220367 | A1 | 11/2003 | Cournoyer et al. |
| 2003/0232877 | A1 | 12/2003 | Sikorski et al. |
| 2004/0006056 | A1 | 1/2004 | Harris et al. |
| 2004/0029933 | A1 | 2/2004 | Zhao et al. |
| 2004/0048858 | A1 | 3/2004 | Sikorski et al. |
| 2004/0102435 | A1 | 5/2004 | Barlaam et al. |
| 2004/0152140 | A1 | 8/2004 | Kelly et al. |
| 2004/0209776 | A1 | 10/2004 | Farooq et al. |
| 2004/0229894 | A1 | 11/2004 | Kerwin et al. |

FOREIGN PATENT DOCUMENTS

| DE | 274490 | 5/1913 |
| DE | 602336 | 8/1934 |
| DE | 2 314 238 | 9/1974 |
| DE | 4208535 | 9/1992 |
| DE | 4304650 | 8/1994 |
| EP | 0 479 161 | 4/1992 |
| EP | 0 611 660 | 8/1994 |
| JP | 04-183754 | 6/1992 |
| JP | 5-17458 | 1/1993 |
| JP | 06-073050 | 3/1994 |
| JP | 06-073051 | 3/1994 |
| JP | 06-239849 | 8/1994 |
| JP | 6336586 | 12/1994 |
| JP | 07-097379 | 4/1995 |
| JP | 09227576 | 9/1997 |
| JP | 09328678 | 12/1997 |
| JP | 09165391 | 6/1999 |
| JP | 2000100569 | 4/2000 |
| JP | 2001055332 | 2/2001 |
| JP | 2001064166 | 3/2001 |

(Continued)

OTHER PUBLICATIONS

Stephens et al. Journal of the Chemical Society 1950, 1722-6.*

(Continued)

*Primary Examiner*—Rebecca L Anderson
*Assistant Examiner*—Jason M Nolan
(74) *Attorney, Agent, or Firm*—Fish & Richardson P.C.

(57) ABSTRACT

Compounds, compositions and methods are provided for stabilizing transthyretin and for treating, preventing, or ameliorating one or more symptoms of transthyretin mediated diseases. In one embodiment, the compounds are benzoxazoles and related compounds.

14 Claims, No Drawings

FOREIGN PATENT DOCUMENTS

| | | |
|---|---|---|
| JP | 2001064205 | 3/2001 |
| JP | 2001242165 | 9/2001 |
| JP | 2001291593 | 10/2001 |
| JP | 2001301329 | 10/2001 |
| JP | 2002003368 | 1/2002 |
| JP | 2004250411 | 9/2004 |
| JP | 2004302049 | 10/2004 |
| WO | WO 98/27972 | 7/1998 |
| WO | WO 00/78733 | 12/2000 |
| WO | WO 01/12183 | 2/2001 |
| WO | WO 01/14354 | 3/2001 |
| WO | WO 01/27088 | 4/2001 |
| WO | WO 01/74786 | 10/2001 |
| WO | WO 02/16333 | 2/2002 |
| WO | WO 02/46168 | 6/2002 |
| WO | WO 02/051821 | 7/2002 |
| WO | WO 03/020698 | 3/2003 |
| WO | WO 03/045930 | 6/2003 |
| WO | WO 03/074516 | 9/2003 |
| WO | WO 03/089418 | 10/2003 |
| WO | WO 2004/046123 | 6/2004 |
| WO | WO 2004/056315 | 7/2004 |
| WO | WO 2004063155 A1 * | 7/2004 |
| WO | WO 2004/064771 | 8/2004 |
| WO | WO 2004/083189 | 9/2004 |
| WO | WO 2004/083195 | 9/2004 |
| WO | WO 2004/084824 | 10/2004 |
| WO | WO 2004/092140 | 10/2004 |
| WO | WO 2004/094395 | 11/2004 |
| WO | WO 2004/098494 | 11/2004 |

OTHER PUBLICATIONS

March, J. Advanced Organic Chemistry John Wiley & Sons, 4th Ed., 1992.*
Morissette et al. Advanced Drug Delivery Reviews 2004, 56, 275-300.*
Sacchettini et al. Nature Reviews Drug Discovery Apr. 2002, 1, 267-275.*
FoldRx Press Release, Jul. 21, 2009.*
Announcement from Business Wire, Nov. 20, 2008.*
www.wrongdiagnosis.com/t/transthyretin_amyloidosis/symptoms.htm, Jul. 21, 2009.*
Schafer et al. Drug Discovery Today 2008, 13 (21/22), 913-916.*
Horig et al. Journal of Translational Medicine 2004, 2(44).*
Hari et al., "Extending the Scope of Chromium-Manganese Redox-Coupled Reactions: A One-Pot Synthesis of Benzoxazoles," J. Org. Chem. (2001), 66:992-996.
Miller, N., "The Misfolding Diseases Unfold", Beremans, Ltd., (2004), pp. 1-4.
Steadman, T. "Stedman's Medial Dictionary" 27th ed., Lippincott Williams & Wilkins, (2000), p. 65.
Aydin et al., "Analgesic and antispasmodic activities of 2-(2-nitrophenyl)-1-$H$-benzimidazole 5-carobxylic acid: evidence for the importance of the 2-($o$-substituted phenyl) group," Pharmazie, vol. 58, No. 6, 2003, pp. 405-408.
Baures et al., "Synthesis and Evaluation of Inhibitors of Transthyretin Amyloid Formation Based on the Non-Steroidal Anit-inflammatory Drug, Flufenamic Acid," Bioorganic & Medicinal Chemistry, vol. 7, 1999, pp. 1339-1347.
Baures et al., "Discovering Transthyretin Amyloid Fribril Inhibitors by Limited Screening," Bioorganic & Medicinal Chemistry, vol. 6, 1998, pp. 1389-1401.
Beaulieu et al., "Non-nucleoside Inhibitors of the Hepatitis C virus NS5B Polymerase: Discovery and Preliminary SAR of Benzimidazole Derivatives," Bioorganic & Medicinal Chemistry Letters, vol. 14, 2004, 119-124.
Essassi et al., "Synthese Et Hererocyclisation Des (Pyrazolyl-3(5))-2 Benzimidazoles En Catalyse Par Transfert De Phase," Bulletin De La Société Chimique Belge, vol. 96, No. 1, 1987, pp. 63-68.

Göker et al., "Synthesis and Antimicrobial Activity of Some New 2-Phenyl-$N$-Substituted Carboxamido-1$H$-benzimidazole Derivatives," Archiv Der Pharmazie, vol. 334, 2001, pp. 148-152.
Green et al., "Synthesis and Characterization of Potent Bivalent Amyloidosis Inhibitors That Bind Prior to Transthyretin Tetramerization," J. Am. Chem. Soc., vol. 125, 2003, pp. 13404-13414.
Hammarström et al., "Prevention of Transthyretin Amyloid Disease by Changing Protein Misfolding Energetics," Science, vol. 299, 2003, pp. 713-713.
Hammarström et al., "Trans-Suppression of Misfolding in an Amyloid Disease," Science, vol. 293, 2001, 2459-2462.
Haskell et al., "Neuraminidase Inhibition and Viral Chemotherapy," Journal of Medicinal chemistry, American Chemical Society, Washington, US, vol. 13, No. 4, Jul. 1970, pp. 697-704.
Hilliard et al., "Multiple Mechanisms of Action for Inhibitors of Histidine Protein Kinases from Bacterial Two-Component Systems," Antimicrobial Agents and Chemotheraphy, vol. 43, No. 7, Jul. 1999, pp. 1693-1699.
Hisano et al., "Synthesis of Organosulfur Compounds. VIII.[1)] Cyclization Products from the Modified Willgerodt-Kindler Reaction[2)]," Chem. Pharmaceutical Bulletin, vol. 21, 1973, pp. 511-517.
Jennings et al., "Efficient Synthesis of (±)-seco-Cyclopropaneindoline Analogs of CC-1065," Heterocyclic Communications, vol. 7, No. 1, 2001, pp. 7-16.
Kelly et al., "The Environment Dependency of Protein Folding Best Explains Prion and Amyloid Diseases," PNAS, vol. 95, PNAS, pp. 930-932, 1998.
Kim et al., "Structure-Activity Relationships of Benzimidazoles and Related Heterocycles as Topoisomerase I Poisons," Bioorganic & Medicinal Chemistry, vol. 4, 1996, pp. 621-630.
Klabunde et al., "Rational Design of Potent Human Transthyretin Amyloid Disease Inhibitors," Nature Structural Biology, vol. 7, No. 4, 2000, pp. 312-321.
Kreimeyer et al., "Suramin analogues with a 2-phenylbenzimidazole moiety as partial structure," Pharmazie, Pharmazeutischer Verl., Eschborn, DE, vol. 52, No. 4, Apr. 1997, pp. 268-271.
Lashuel et al., "New Class of Inhibitors of Amyloid-beta Fibril Formation," J. Biol. Chem., vol. 277, No. 45, 2002, pp. 42881-42890.
Lee et al., "Solid-phase combinatorial synthesis of benzothiazole and 2,3-dihydro-[1,5]-benzothiazepine derivatives," Tetrahedron Letters, Elsevier Science Publishers, Amsterdam, NL, vol. 42, No. 1, Jan. 2001, pp. 109-111.
Lin et al., "Bioisosteric Replacement of Anilide with Benzoxazole: Potent and Orally Bioavailable Antagonists of VLA-4," Bioorganic and Medicinal Chem. Letters, vol. 14, 2004, pp. 2331-2334.
Miroy et al., "Inhibiting Transthyretin Amylid Fibril Formation Via Protein Stabilization," PNAS, vol. 93, 1996, pp. 15051-15056.
Oza et al., "Sythesis and Evaluation of Anthranilic Acid-Based Transthyretin Amylid Fribril Inhibitors," Bioorganic & Medicinal Chemistry Letters, vol. 9, 1999, pp. 1-6.
Oza et al., "Synthesis, Structure, and Activity of Diclofenac Analogues as Transthyretin Amyloid Fibril Formation Inhibitors," J. Med. Chem., vol. 45, 2002, 321-332.
Peterson et al., "Inhibiting Transthyretin Conformational Changes That Lead to Amyloid Firbril Formation, " PNAS, vol. 95, 1998, pp. 12956-12960.
Petrassi et al., "Structure-Based Design of N-Phenyl Phenoxazine Transthyretin Amyloid Fibril Inhibitors," J. Am. Chem. Soc., vol. 122, No. 10, 2000, pp. 2178-2192.
Purkey et al., "Evaluating the Binding Selectivity of Transthyretin Amyloid Fibril Inhibitors in Blood Plasma," PNAS, vol. 98, No. 10, 2001, pp. 5566-5571.
Razavi et al., "Benzoxazoles as Transthyretion Amyloid Fribril Inhibitors: Synthesis, Evaluation, and Mechanism of Action," Angew Chem Int Ed. vol. 42, 2003, pp. 2758-2761.
Rtishchev et al., "Absorption and Luminescence in the series of 2-Phenylbenzothiazole and Related Compounds," Russ. Journal of Gen. Chemistry, vol. 63, No. 2.2, 1993, pp. 303-309.
Sacchettini et al., "Therapeutic Strategies for Human Amyloid Diseases," Nature Reviews, vol. 1, 2002, pp. 267-275.
Singh et al., "Synthetic Utility of Catalytic Fe(III)/Fe(II) Redox cycling Towards Fused Heterocycles: A Facile Access to Substituted Benzimidazole, Bis-benzimidazole and Imidazophyridine Derivatives," Synthesis, No. 10, 2000, pp. 1380-1390.

Stephens et al., "The Preparation of Benziminazoles and Benzoxazoles from Schiff's Bases, Part II," Journal of the chemical Society, Chemical Society, Letchworth, GB, 1950, pp. 1722-1726.

Xue et al., "Design, Synthesis and In Vitro Activities of a Series of Benzimidazole/Benzoxazole Glycoprotein IIb/IIIa Inhibitors," Bioorganic & Medicinal Chemistry Letters, Oxford, GB, vol. 6, No. 3, 1996, pp. 339-344.

"Orphan amyloid diseases," Nature Structural Biology, vol. 7, No. 4, 2000, pp. 259-260.

Biot et al., "5-Substituted Tetrazoles as Bioisoteres of Carboxylic Acids. Bioisosterism and Machnistic Studies on Glutathione Reductase Inhibitors as Antimalarials," *J. Med. Chem.*, 47:5972-5983 (2004).

Costantino et al., "Synthesis and Biological Evaluation of 2-(3'-(1H-Tetrazol-5-yl)bicycle[1.1.1]pent-1-yl)glycine (S-TBPG), a Novel mGlu1 Receptor Antagonist," *Bio & Med. Chem.*, 9:221-227 (2001).

Desos, et al., "Structure-Activity Relationships in a Series of 2(1H)-Quinolones Bearing Difference Acidic Function in the 3-Position: 6,7-Dichloro-2(1H)-oxoquinoline-3-phosphonic Acid, a New Potent and Selective AMPA/Kainate Antagonist with Neuroprotective Properties," *J. Med. Chem.*, 39:197-206 (1996).

Dawson et al., "An Adamantyl-Substituted Retinoid-Derived Molecule That Inhibits Cancer Cell Growth and Angiogenesis by Inducing Apoptosis and Binds to Small Heterodimer Partner Nuclear Receptor: Effects of Modifying Its Carboxylate Group on Apoptosis, Proliferation, and Protein-Tyrosine Phosphatase Activity," *J. Med. Chem.*, 50:2622-2639 (2007).

Faucher et al., "Discovery of Small-Molecule Inhibitors of the ATPase Activity of Human Papillomavirus E1 Helicase," *J. Med. Chem.*, 47:18-21 (2004).

Goker et al., "Synthesis of 1,2—Disubstituted Benzimidazole-5(6)-Carboxamides and Evaluation of Their Antimicrobial Activity," *Farmaco, Societa Clinica Italiana*, 51:1: 53-58 (1995).

Hansch, "Notes on the Design of Bioactive Compounds," *Am. Chem. Soc.*, Chapter 13, 513-543 (1995).

Herr, "5-Substituted-1H-tetrazoles as Carboxylic Acid Isosteres: Medicinal Chemistry and Synthetic Methods," *Bio & Med. Chem.*, 10:3379-3393 (2002).

Huskey et al., "N-Glucuronidation Reactions. I. Tetrazole N-Glucuronidation of Selected Angiotensin II Receptor Antagonists in Hepatic Microsomes from Rats, Dogs, Monkeys, and Humans," *Drug Met. And Dis.*, 21:5: 792-799 (1993).

Kraus, "Isosterism and Molecular Modification in Drug Design: Tetrazole analogue of GABA: Effects on enzymes of the γ-aminobutyrate system," *Pharma. Res. Comm.*, 15:2:183-189 (1983).

Larsen et al., "Design and application of prodrugs," Chapter 14, 410-458 (2002).

Myznikov, et al., "Drugs in the Tetrazole Series," *Chem of Het. Com.*, 43:1 (2007).

Razavi et al., "Benzoxazoles as Transthyretin Amyloid Fibril Inhibitors: Synthesis, Evaluation, and Mechanism of Action," *Angew. Chem.*, 115: 2864-2867 (2003).

Stearns, "Synthesis and Identification of a Novel Tetrazole Metabolite of the Angiotensin II Receptor Antagonist DuP 753," *Drug Met. And Dis.*, 19:6: 1160-1162 (1991).

Office Action from EP 05 751 051.3-2101, mailed Feb. 2, 2008 (6 pages).

Lobell et al., *Molecular Diversity*, 7, 2003, pp. 69-87.

Guzow et al., "Influence of an aromatic substituent in position 2 on photophysical properties of benzoxazol-5-yl-alanine derivatives," *Chem. Phys.*, 2003, 295(2):119-130.

Rzeska et al., "New highly fluorescent amino-acid derivatives substituted 3-[2-(phenyl)benzoxazol-5-yl]-alanines:synthesis and photophysical properties," *J. Photochem. Photobiol. A:Chemistry*, 2001, 146:9-18.

Guzow et al., "Influence of an aromatic substituent in position 2 on photophysical properties of benzoxazol-5-yl-alanine derivatives," Chemical Physics, 295: 119-130 (2003).

Rzeska et al., "Substituted 3-{2-(phenyl)benzoxazol-5-yl}-alanines: synthesis and photophysical properties," Journal of Photochemistry and Photobiology, 146: 9-18 (2001).

EPO Communication pursuant to Article 94(3) EPC for EP Application No. 05751051.3, dated Feb. 7, 2008, 7 pages.

EPO Reply to Communication to Article 94(3) EPC for EP Application No. 05751051.3, dated Jun. 16, 2008, 57 pages.

EPO Communication pursuant to Article 94(3) EPC for EP Application No. 05751051.3, dated Dec. 1, 2008, 22 pages.

EPO Request for Voluntary Amendment pursuant to Rule 137(3) EPC for EP Application No. 05751051.3, dated Oct. 14, 2008, 19 pages.

Chu-Biao X et al., *Bioorganic & Medicinal Chemistry Letters*, vol. 6, No. 3; 1996; pp. 339-344.

Lavoie, et al., "Structure-activity relationships of benzimidazoles and related heterocycles as topoisomerase I poisons," *Bioorganic & Medicinal Chemistry*, vol. 4, No. 4; 1996; pp. 621-630.

Lima et al, "Bioisosterism: A Useful Strategy for Molecular Modification and Drug Design," *Current Medicinal Chemistry*, vol. 12; 2005; pp. 23-49.

EPO Communication Pursuant to Article 94(3) EPC, dated Jul. 19, 2010 for EP Application No. 05751051.3-2101; 5 pages.

PCT International Search Report and Written Opinion, dated Sep. 12, 2005 for PCT International Application No. PCT/US2005/017612; 157 pages.

\* cited by examiner

COMPOUNDS, COMPOSITIONS AND METHODS FOR STABILIZING TRANSTHYRETIN AND INHIBITING TRANSTHYRETIN MISFOLDING

RELATED APPLICATION

Priority is claimed herein under 35 U.S.C. 119(e) to U.S. provisional patent application Ser. No. 60/573,720, filed May 20, 2004, entitled "COMPOUNDS, COMPOSITIONS AND METHODS FOR STABILIZING TRANSTHYRETIN AND INHIBITING TRANSTHYRETIN MISFOLDING." The disclosure of the above-referenced application is incorporated by reference herein in its entirety.

FIELD

Provided herein are compounds, compositions and methods relating generally to protein misfolding. More particularly, provided herein are benzoxazole compounds, compositions and methods for stabilizing transthyretin, inhibiting transthyretin misfolding, inhibiting transthyretin fibril and amyloid formation and treating amyloid diseases associated thereto.

BACKGROUND

Transthyretin (TTR) is a 55 kDa homotetrameric protein present in serum and cerebral spinal fluid. The function of TTR is to transport L-thyroxine ($T_4$) and holo-retinol binding protein (RBP). TTR is one of greater than 20 nonhomologous amyloidogenic proteins that can be transformed into fibrils and other aggregates leading to disease pathology in humans. These diseases do not appear to be caused by loss of function due to protein aggregation. Instead, aggregation appears to cause neuronal/cellular dysfunction by a mechanism that is not yet clear.

Under denaturing conditions, rate limiting wild type TTR tetramer dissociation and rapid monomer misfolding enables misassembly into amyloid, putatively causing senile systemic amyloidosis (SSA). Dissociation and misfolding of one or more than eighty TTR variants results in a wide variety of familial amyloidoses, including familial amyloid polyneuropathy (FAP) and familial amyloid cardiomyopathy (FAC).

The TTR tetramer has two $C_2$ symmetric $T_4$-binding sites. Negatively cooperative binding of $T_4$ is known to stabilize the TTR tetramer and inhibit amyloid fibril formation. Unfortunately, less than 1% of TTR has $T_4$ bound to it in the human serum, because thyroid-binding globulin (TBG) has an order of magnitude higher affinity for $T_4$ in comparison to TTR. Furthermore, the serum concentration of $T_4$ is relatively low (0.1 µM) compared to that of TTR (3.6-7.2 µM).

SUMMARY

Provided herein are compounds that kinetically stabilize the native state of transthyretin, thereby inhibiting protein misfolding. Protein misfolding plays a role in a variety of disease processes, including transthyretin amyloid diseases. By inhibiting transthryetin misfolding, one can intervene in or treat such a disease, ameliorate symptoms, and/or in some cases prevent or cure the disease.

The compounds, compositions and methods described herein for treating, preventing, or ameliorating one or more symptoms of TTR amyloidosis. TTR amyloidosis typically leads to death in 5 to ten years, and until recently, was considered incurable. Liver transplantation is an effective means of replacing the disease-associated allele by a wild-type (WT) allele in familial amyloid polyneuropathy cases because the liver is typically the source of amyloidogenic TTR. While liver transplantation is effective as a form of gene therapy it is not without its problems. Transplantation is complicated by the need for invasive surgery for both the recipient and the donor, long-term post-transplantation immunosuppressive therapy, a shortage of donors, its high cost, and the large number of TTR amyloidosis patients that are not good candidates because of their disease progression. Unfortunately, cardiac amyloidosis progresses in some familial patients even after liver transplantation because WT TTR often continues to deposit. Nor is central nervous system (CNS) deposition of TTR relieved by transplantation owing to its synthesis by the choroid plexus. Transplantation is not a viable option for the most prevalent TTR diseases, senile systemic amyloidosis (SSA), affecting approximately up to 25% of those over 80 due to the deposition of WT TTR and for familial cardiac amyloidosis, including carriers of V122I, a mutant identified in 3.9% of African Americans.

In one embodiment, the compounds for use in the compositions and methods provided herein have formulae I:

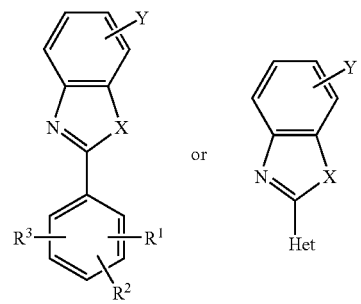

where Y is COOH, $COOR^5$, $CONR^7R^8$, tetrazolyl, CONHOH, $B(OH)_2$, $CONHSO_2Ar$, $CONHCH(R^6)COOH$, OH, $CH_2OH$ or $—(CH_2)_n—C(R^6)(NH_2)—COOH$;

X is O, S or $NR^{11}$;

$R^1$, $R^2$ and $R^3$ are each independently selected from hydrogen, halo, $OR^5$, OAr, OHet, $OCH_2Ar$, $OCH_2Het$, CN, $B(OH)_2$, COOH, $CONR^7R^8$, alkyl, haloalkyl, $—(CR^9R^{10})_nOH$, $—(CR^9R^{10})_nNR^7R^8$, $—(CR^9R^{10})_nSH$ or $CF_3$;

Het is heteroaryl, optionally substituted with halo, OR, alkyl or haloalkyl;

Ar is aryl, optionally substituted with halo, OR, alkyl or haloalkyl;

R is hydrogen, alkyl, alkenyl, alkynyl, cycloalkyl, heterocyclyl, aryl or heteroaryl;

$R^5$ is alkyl, haloalkyl, cycloalkyl, heterocyclyl or aralkyl;

$R^6$ is the side chain of a naturally occurring α-amino carboxylic acid;

$R^7$ and $R^8$ are each independently hydrogen, alkyl, alkenyl, alkynyl, cycloalkyl, heterocyclyl, aryl or heteroaryl;

$R^9$ and $R^{10}$ are each independently hydrogen, halo, alkyl, alkenyl, alkynyl, cycloalkyl, heterocyclyl, aryl or heteroaryl;

$R^{11}$ is hydrogen or alkyl; and n is an integer from 0-3.

In one embodiment, Het is pyrimidinyl, pyridyl, furyl or thienyl. In another embodiment, Het is pyridyl.

In another embodiment, $R^1$, $R^2$ and $R^3$ are each independently selected from hydrogen, halo, $OR^5$, OAr, OHet, $OCH_2Ar$, $OCH_2Het$, CN, $B(OH)_2$, COOH, $CONR^7R^8$, alkyl, $-(CR^9R^{10})_nOH$, $-(CR^9R^{10})_nNR^7R^8$, $-(CR^9R^{10})_nSH$ or $CF_3$.

In one embodiment, the compounds have formulae I, with the proviso that when Y is COOH and is in the 4, 5, 6 or 7 position, then $R^1$, $R^2$ and $R^3$ are not Cl, F or $CF_3$. In another embodiment, the compounds have formulae I, with the proviso that when Y is COOH and is in the 4, 5, 6 or 7 position, then $R^1$, $R^2$ and $R^3$ are not 3,5-difluoro, 2,6-difluoro, 2- or 3-trifluoromethyl, 3,5-dichloro or 2,6-dichloro. In another embodiment, the compounds have formulae I, with the proviso that when Y is COOH and is in the 4, 5, 6 or 7 position, then $R^1$, $R^2$ and $R^3$ are not all hydrogen. In another embodiment, the compounds have formulae I, with the proviso that when Y is COOH or $CONH_2$, then $R^1$, $R^2$ and $R^3$ are not alkyl, cycloalkyl, alkoxy, COOH, COOR where R is alkyl or OH. In another embodiment, the compounds have formulae I, with the proviso that when Y is COOH and X is NH, then $R^1$, $R^2$ and $R^3$ are not 4-CN. In another embodiment, the compounds have formulae I, with the proviso that when Y is COOH, then $R^1$, $R^2$ and $R^3$ are not CN. In another embodiment, the compounds have formulae I, with the proviso that when Y is COOH or $CONH_2$, then $R^1$, $R^2$ and $R^3$ are not alkyl, alkoxy, cycloalkoxy or CN. In another embodiment, the compounds have formulae I, with the proviso that when Y is COOH or $CONH_2$, then $R^1$, $R^2$ and $R^3$ are not 3-, 4-, or 5-alkyl, 4-alkoxy or 4-cycloalkoxy.

Also provided herein are pharmaceutical compositions containing the compounds provided herein.

Also provided are methods for the stabilization of transthyretin in a tissue or in a biological fluid, and thereby inhibiting misfolding. Generally, the method involves administering to the tissue or biological fluid a stabilizing amount of a compound provided herein that binds to transthyretin and prevents dissociation of the transthyretin tetramer by kinetic stabilization of the native state of the transthyretin tetramer.

Thus, methods which stabilize transthyretin in a diseased tissue ameliorate misfolding and lessen symptoms of an associated disease and, depending upon the disease, can contribute to cure of the disease. Also contemplated herein is inhibition of transthyretin misfolding in a tissue and/or within a cell. The extent of misfolding, and therefore the extent of inhibition achieved by the present methods, can be evaluated by a variety of methods, such as are described in the Examples and in international patent application publication no. WO2004/056315. The disclosure of the above-referenced application is incorporated herein by reference in its entirety.

Also provided herein is a method of treating, preventing, or ameliorating one or more symptoms of a transthyretin amyloid disease, the method involving administering a therapeutically effective amount of a compound provided herein. In one embodiment, the compound prevents dissociation of a transthyretin tetramer by kinetic stabilization of the native state of the transthyretin tetramer. The transthyretin amyloid disease can be, for example, familial amyloid polyneuropathy, familial amyloid cardiomyopathy, or senile systemic amyloidosis. Other transthyretin amyloid diseases include but are not limited to Alzheimer's disease, spongiform encephalopathy (Creutzfeldt Jakob disease), polyneuropathy, type II diabetes and medullary carcinoma of the thyroid (see, e.g., International Patent Application Publication Nos. WO 98/27972 and WO 95/12815).

Methods of treating, preventing, or ameliorating one or more symptoms of a transthyretin mediated disease or disorder by administering a compound provided herein are provided. Transthyretin mediated diseases and disorders include but are not limited to obesity (see, e.g., International Patent Application Publication No. WO 02/059621).

Further provided is a method of stabilizing TTR tetramers using a compound or composition provided herein. Also provided is a method of inhibiting formation of TTR amyloid using a compound or composition provided herein.

Also provided herein is use of any of the compounds or pharmaceutical compositions described herein for the treatment, prevention, or amelioration of one or more symptoms of a transthyretin amyloid disease (e.g., familial amyloid polyneuropathy, familial amyloid cardiomyopathy, or senile systemic amyloidosis).

Also provided herein is use of any of the compounds or pharmaceutical compositions described herein in the manufacture of a medicament for the treatment, prevention, or amelioration of one or more symptoms of a transthyretin amyloid disease (e.g., familial amyloid polyneuropathy, familial amyloid cardiomyopathy, or senile systemic amyloidosis).

Articles of manufacture, containing packaging material, a compound or pharmaceutically acceptable derivative thereof provided herein, which is effective for preventing TTR misfolding, or for treatment, prevention or amelioration of one or more symptoms of diseases or disorders associated with TTR misfolding, or diseases or disorders in which TTR misfolding, is implicated, within the packaging material, and a label that indicates that the compound or composition, or pharmaceutically acceptable derivative thereof, is used for modulating TTR folding, or for treatment, prevention or amelioration of one or more symptoms of diseases or disorders associated with TTR misfolding, or diseases or disorders in which TTR misfolding is implicated, are also provided.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, transthyretin or TTR is a 55 kDa homotetramer characterized by 2,2,2 symmetry, having two identical funnel-shaped binding sites at the dimer-dimer interface, where thyroid hormone (T4) can bind in blood plasma and CSF. TTR is typically bound to less than 1 equiv of holo retinol binding protein. TTR is a 127-residue protein that tetramerizes under physiological conditions. TTR serves as the tertiary transporter of thyroxine in the serum and the primary carrier in the cerebrospinal fluid. TTR also transports retinol through its association with retinol binding protein. TTR forms amyloid at low pH.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Other pharmaceutically acceptable salts include acid salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate; base salts including ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained. Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, or cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating TTR mediated diseases or disorders, or diseases or disorders in which TTR, including TTR misfolding, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as inhibition of TTR misfolding, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl andl-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)2-.
As used herein, "sulfo" refers to —S(O)2O—.

As used herein, "carboxy" refers to a divalent radical, —C(O)O—.

As used herein, "aminocarbonyl" refers to —C(O)NH2.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)2 groups, or substituted or unsubstituted nitrogen atoms, including —NR— and —N+RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH2-), ethylene (—CH2CH2-), propylene (—(CH2)3-), methylenedioxy (—O—CH2-O—) and ethylenedioxy (—O—(CH2)2-O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)n-NR—(CRR)m-, where n and m are each independently an integer from 0 to 4. As used herein, "oxaalkylene" refers to —(CRR)n-O—(CRR)m-, where n and m are each independently an integer from 0 to 4. As used herein, "thiaalkylene" refers to —(CRR)n-S—(CRR)m-, —(CRR)n-S(=O)—(CRR)m-, and —(CRR)n-S(=O)2-(CRR)m-, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH2-. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH2-. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C≡C—(CH2)n-C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from Q1.

As used herein, "alkylidene" refers to a divalent group, such as =CR'R", which is attached to one atom of another group, forming a double bond. Alkylidene groups include, but are not limited to, methylidene (=CH2) and ethylidene (=CHCH3). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO2NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens. As another example, "C1-3alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:942-944).

B. TTR and Amyloid Disease

At least some amyloid diseases appear to be caused by the deposition of any one of more than 20 nonhomologous proteins or protein fragments, ultimately affording a fibrillar cross-β-sheet quaternary structure. Formation of amyloid fibrils from a normally folded protein like transthyretin requires protein misfolding to produce an assembly-competent intermediate. The process of transthyretin (TTR) amyloidogenesis appears to cause three different amyloid diseases—senile systemic amyloidosis (SSA), familial amyloid polyneuropathy (FAP) and familial amyloid cardiomyopathy (FAC). SSA is associated with the deposition of wild-type TTR, while FAP and FAC are caused by the amyloidogenesis of one of over 80 TTR variants. See, for example, Colon, W.; Kelly, J. W. *Biochemistry* 1992, 31, 8654-60; Kelly, J. W. *Curr. Opin. Struct. Biol.* 1996, 6, 11-7; Liu, K.; et al. *Nat. Struct. Biol.* 2000, 7, 754-7; Westermark, P.; et al. *Proc. Natl. Acad. Sci. U.S.A.* 1990, 87, 2843-5; Saraiva, M. J.; et al. *J. Clin. Invest.* 1985, 76, 2171-7; Jacobson, D. R.; et al. *N. Engl. J. Med.* 1997, 336, 466-73; Buxbaum, J. N.; Tagoe, C. E. *Ann. Rev. Med.* 2000, 51, 543-569; and Saraiva, M. J. *Hum. Mutat.* 1995, 5, 191-6, each of which is incorporated by reference in its entirety.

TTR is a 55 kDa homotetramer characterized by 2,2,2 symmetry, having two identical funnel-shaped binding sites at the dimer-dimer interface, where thyroid hormone (T4) can bind in blood plasma and CSF. TTR is typically bound to less than 1 equiv of holo retinol binding protein. TTR misfolding including tetramer dissociation into monomers followed by tertiary structural changes within the monomer render the protein capable of misassembly, ultimately affording amyloid. The available treatment for FAP employs gene therapy mediated by liver transplantation to replace variant TTR in the blood with the wild type (WT) protein. This treatment is not applicable to most patients with FAC or SSA because of most are over the age of 60 and are not candidates for liver transplantation due to their health status and impaired cardiac function. Furthermore, for several TTR variants associated with FAP, progressive cardiac amyloidosis developed after liver transplantation with wt TTR deposition in cardiac tissues, leading to death. Liver transplantation therapy would also fail for approximately 10 of the TTR variants that deposit amyloid fibrils in the leptomeninges leading to CNS disease, as this TTR is synthesized by the choroid plexus. Hence, it is desirable to develop a general noninvasive drug-based therapeutic strategy. It can be desirable for the drug to be non-protein, non-peptide, or non-nucleic acid based. See, for example, Blake, C. C.; et al. *J. Mol. Biol.* 1978, 121, 339-56; Wojtczak, A.; et al. *Acta Crystallogr., Sect. D* 1996, 758-810; Monaco, H. L.; Rizzi, M.; Coda, A. *Science* 1995, 268, 1039-41; Lai, Z.; Colon, W.; Kelly, J. W. *Biochemistry* 1996, 35, 6470-82; Holmgren, G.; et al. *Lancet* 1993, 341, 1113-6; Suhr, O. B.; Ericzon, B. G.; Friman, S. *Liver Transpl.* 2002, 8, 787-94; Dubrey, S. W.; et al. *Transplantation* 1997, 64, 74-80; Yazaki, M.; et al. *Biochem. Biophys. Res. Commun.* 2000, 274, 702-6; and Cornwell, C. G. III; et al. *Am. J. of Med.* 1983, 75, 618-623, each of which is incorporated by reference in its entirety.

C. Compounds

In one embodiment, the compounds for use in the compositions and methods provided herein have formula IA:

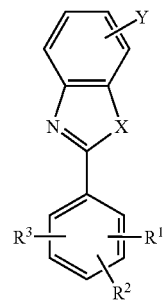

where Y is COOH, tetrazolyl, CONHOH, B(OH)$_2$ or OH;
X is O; and
R$^1$, R$^2$ and R$^3$ are each independently selected from hydrogen, halo, OH, B(OH)$_2$ or CF$_3$.

In another embodiment, the compounds have formulae I, where Y is COOH. In another embodiment, Y is tetrazolyl, B(OH)$_2$ or CONHOH. In another embodiment, Y is OH.

In another embodiment, the compounds have formulae I, where R$^1$, R$^2$ and R$^3$ are each independently selected from hydrogen, halo and OH. In another embodiment, the compounds have formulae I, where R$^1$, R$^2$ and R$^3$ are each independently selected from hydrogen and CF$_3$. In another embodiment, the compounds have formulae I, where R$^1$ and R$^2$ are each independently hydrogen and R$^3$ is CF$_3$. In another embodiment, the compounds have formulae I, where R$^1$, R$^2$ and R$^3$ are each independently selected from hydrogen, halo and B(OH)$_2$. In another embodiment, the compounds have formulae I, where R$^1$, R$^2$ and R$^3$ are each independently selected from hydrogen, Br and I. In another embodiment, the compounds have formulae I, where R$^1$, R$^2$ and R$^3$ are each independently selected from halo and OH. In another embodiment, the compounds have formulae I, where R$^1$, R$^2$ and R$^3$ are each independently selected from halo and B(OH)$_2$. In another embodiment, the compounds have formulae I, where R$^1$ and R$^2$ are each halo and R$^3$ is OH. In another embodiment, the compounds have formulae I, where R$^1$ and R$^2$ are each halo and R$^3$ is B(OH)$_2$. In another embodiment, the compounds have formulae I, where R$^1$ and R$^2$ are each halo and R$^3$ is H.

In another embodiment, the compounds of formulae I have the formulae:

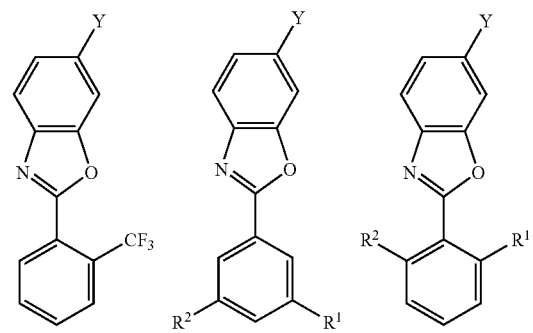

-continued
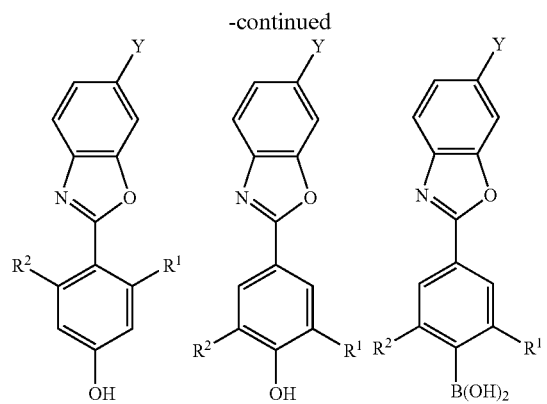
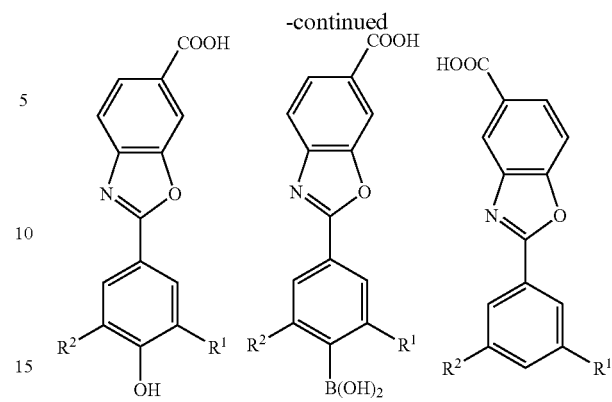
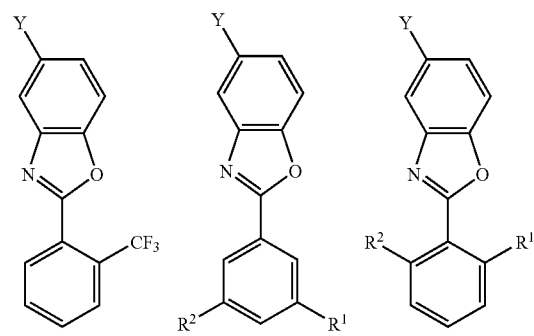
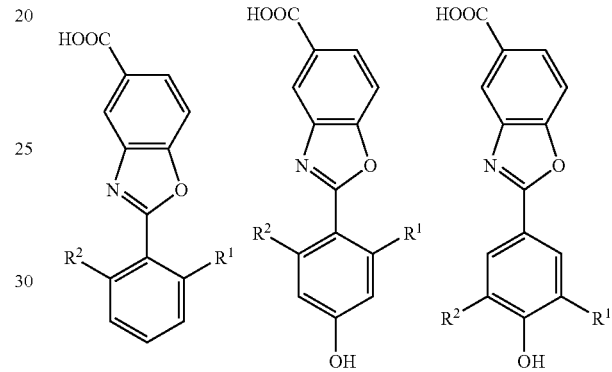
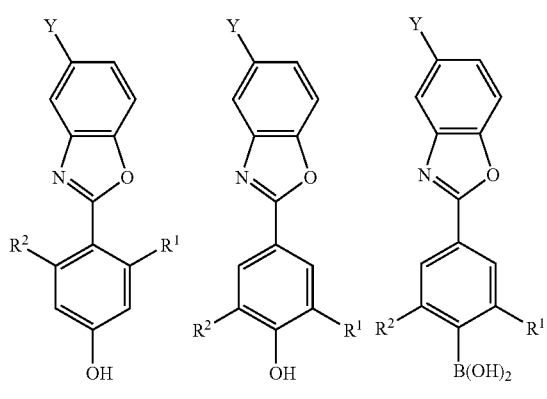
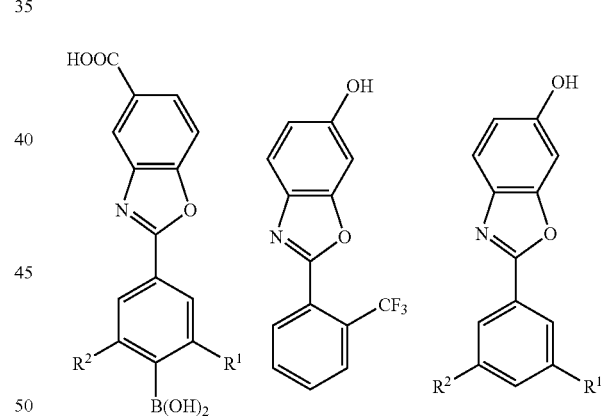
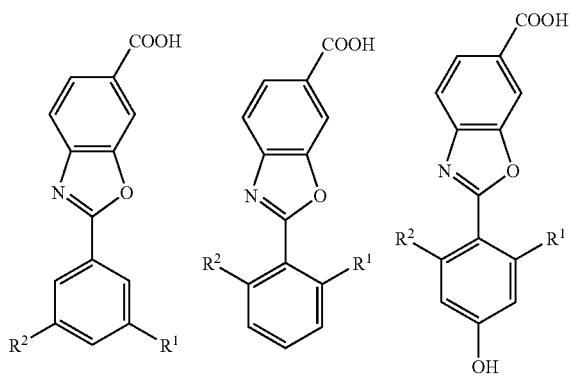
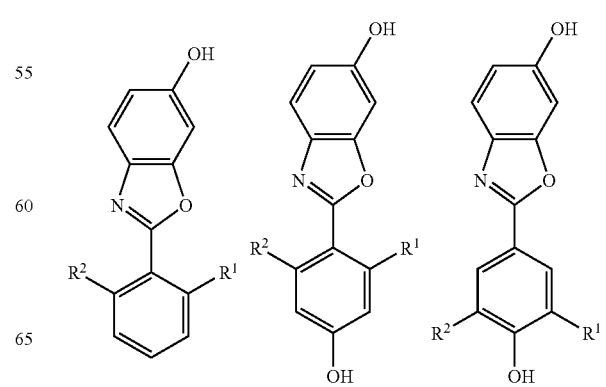

-continued
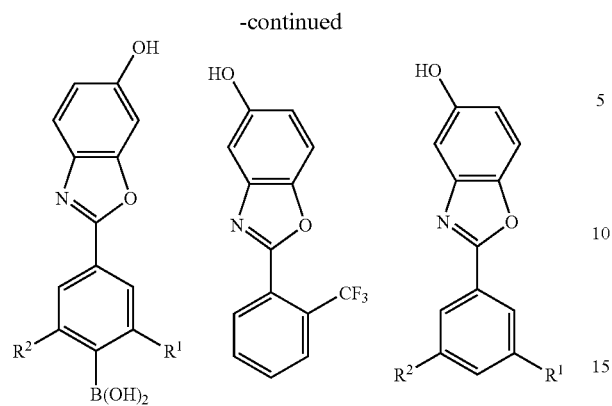
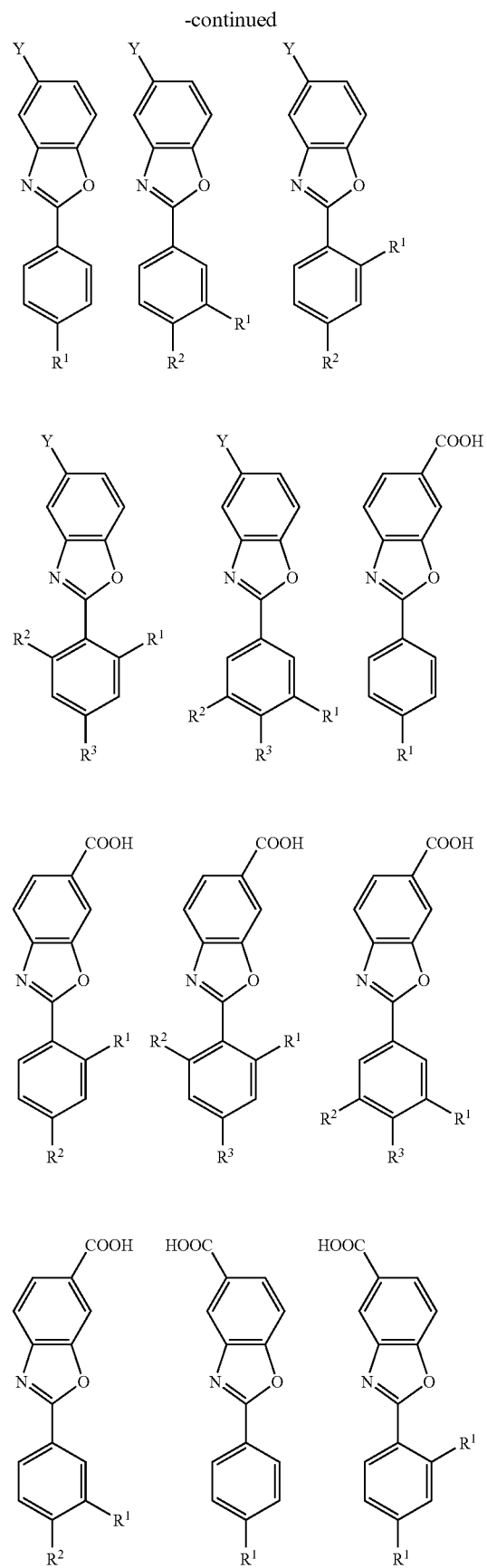

-continued

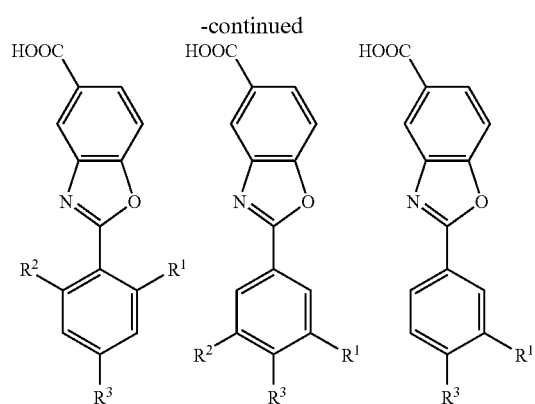
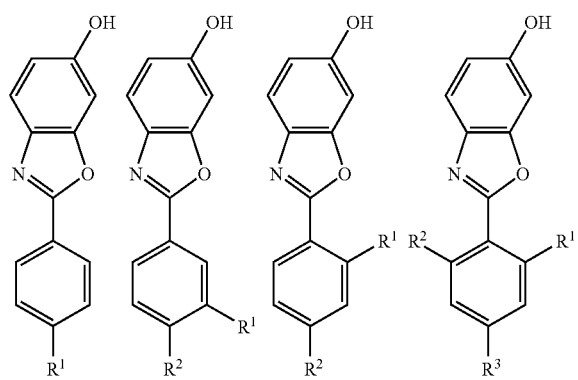
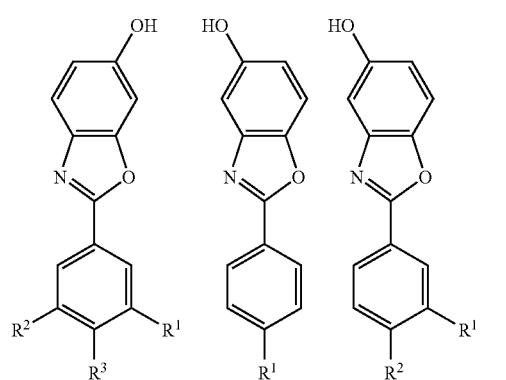

In another embodiment, the compounds provided herein have the formula:

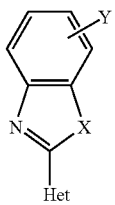

or a pharmaceutically acceptable derivative thereof, wherein Het, X and Y are as defined elsewhere herein.

In another embodiment, Het is 3- or 4-pyridyl, optionally substituted with halo, OR, alkyl or haloalkyl, where R is hydrogen, alkyl, alkenyl, alkynyl, cycloalkyl, heterocyclyl aryl or heteroaryl. In another embodiment, Het is 3- or 4-pyridyl, optionally substituted with halo, alkyl or haloalkyl. In another embodiment, Het is 3- or 4-pyridyl, optionally substituted with trifluoromethyl, chloro or methyl.

In another embodiment, the compounds provided herein are selected from:

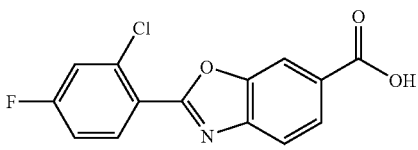
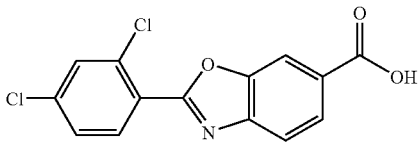
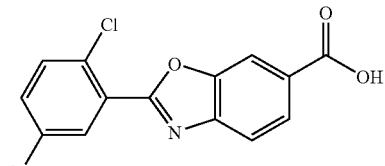
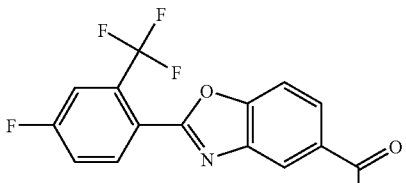
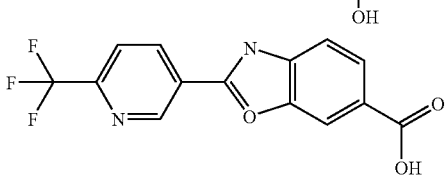
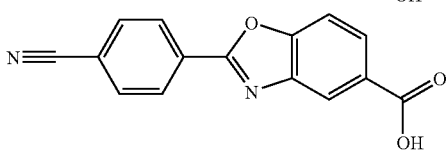

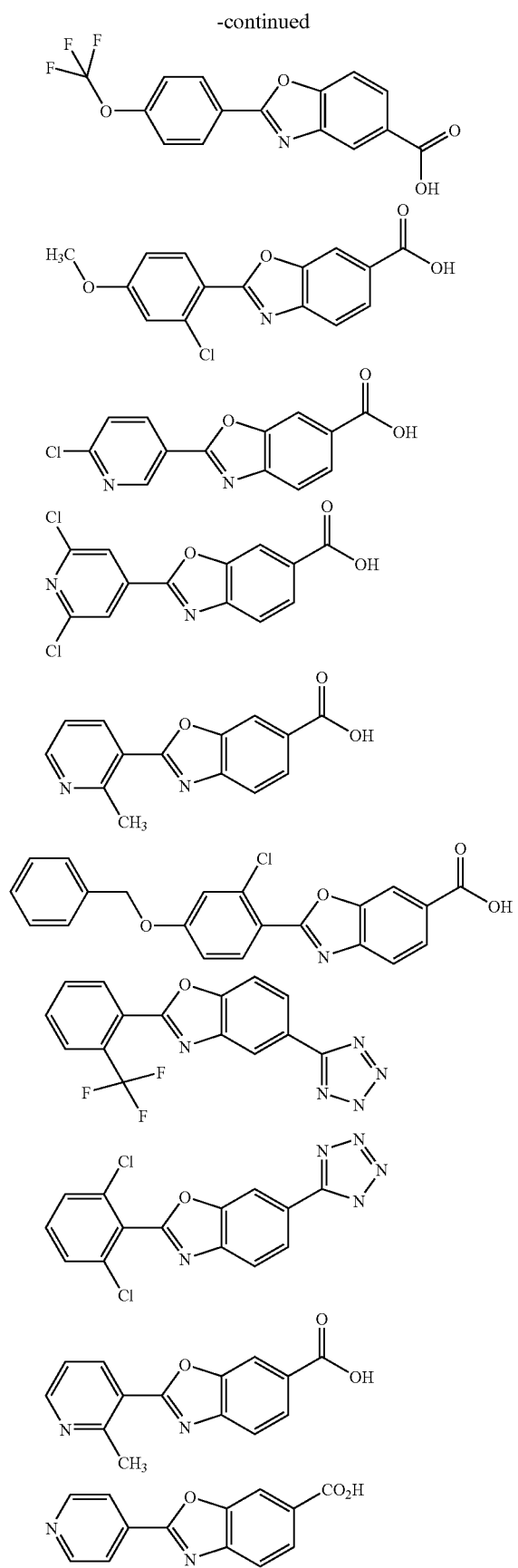

D. Preparation of the Compounds

The compounds provided herein may be made by the methods shown below and in the Examples, or by other methods well known to those of skill in the art. Starting materials in these synthetic methods may be obtained from commercial sources (e.g., Aldrich Chemical Co., Milwaukee, Wis., USA).

Reagents and solvents were purchased from Aldrich, Lancaster, Acros, Combi-Blocks, Matrix and Pfaltz-Bauer. THF and $CH_2Cl_2$ were dried by passage over $Al_2O_3$. Other solvents and reagents were obtained from commercial suppliers and were used without further purification unless otherwise noted. Reactions were monitored by analytical thin layer chromatography (TLC) on silica gel 60 $F_{254}$ pre-coated plates with fluorescent indicator purchased from EM Science. Visualization of the TLC plates was accomplished by UV illumination, phosphomolybdic acid treatment followed by heat or ceric ammonium molybdate treatment followed by heat. Flash chromatography was performed using silica gel 60 (230-400 mesh) from EM Science. The purity of new compounds that were essential to the conclusions drawn in the text were determined by HPLC. Normal phase HPLC was performed with a Waters 600 pump/controller, a Waters 996 photodiode array detector and a Waters NovaPak silica column. The solvent system employed was hexanes and ethyl acetate, and gradients were run from 50:50 hexanes:ethyl acetate to 0:100 hexanes:ethyl acetate over 30 min. Reverse phase HPLC was performed with a Waters 600 pump/controller, a Waters 2487 dual wavelength detector and a Vydac protein and peptide C18 column. Solvent system A was 95:5 water:acetonitrile with 0.5% trifluoroacetic acid and solvent B was 5:95 water:acetonitrile with 0.5% trifluoroacetic acid. Gradients were run from 100:0 A:B to 0:100 A:B over 20 min with a hold at 100% B for an additional 10 min. Circular dichroism spectroscopy was performed on an AVIV Instruments spectrometer, model 202SF. NMR spectra were recorded on a Varian FT NMR spectrometer at a proton frequency of 400 MHz. Proton chemical shifts are reported in parts per million (ppm) with reference to $CHCl_3$ as the internal chemical shift standard (7.26 ppm) unless otherwise noted. Coupling constants are reported in hertz (Hz). Carbon chemical shifts are reported in parts per million (ppm) with reference to CDCl₃ as the chemical shift standard (77.23 ppm) unless otherwise noted.

General Procedure for Benzoxazole Synthesis

A mixture of amino hydroxybenzoic acid (0.2 mmol) in THF (3 mL) was sequentially treated with pyridine (500 µl, 0.6 mmol) and the desired acid chloride (0.2 mmol). The reaction mixture was stirred at ambient temperature for 10 h, refluxed for 1 h, concentrated in vacuo and used in the next step without purification.

p-Toluenesulfonic acid monohydrate (380.4 mg, 2.0 mmol) was added to the crude reaction mixture in xylenes (5 mL) and the resulting mixture was stirred at reflux overnight. After 12 h, the reaction was cooled to ambient temperature, quenched with NaOH (2 mL, 1 N) and the phases were separated. The aqueous layer was acidified with HCl (1 N) to pH 2 and extracted with EtOAc (4×3 mL). The combined organic layers were dried over MgSO₄, filtered and concentrated in vacuo. The resulting residue was dissolved in a mixture of MeOH:Benzene (2 mL; 1:4), treated with TMS-CHN₂ (200 µL of 2.0 M solution in hexanes, 0.4 mmol) at 25° C. and the reaction progress was monitored by TLC (usually complete after 0.5 h). The reaction mixture was concentrated in vacuo, and the residue was chromatographed (10 to 25% EtOAc/hexanes gradient) to afford the desired benzoxazole methyl ester.

The benzoxazole methyl ester was dissolved in a mixture of THF:MeOH:H₂O (3:1:1, 0.07 M) and treated with LiOH.H₂O (4 equiv). The reaction was stirred at ambient temperature and monitored by TLC. Upon completion, the mixture was acidified to pH 2 with 1 N HCl and extracted with EtOAc (4×). The combined organic layers were dried over MgSO₄, filtered and concentrated. The residue was purified by preparative thin layer chromatography (4.9% MeOH, 95% CH₂Cl₂, 0.1% HOAc) to give the product as a white solid.

Alternatively, the compounds may be prepared as shown below:

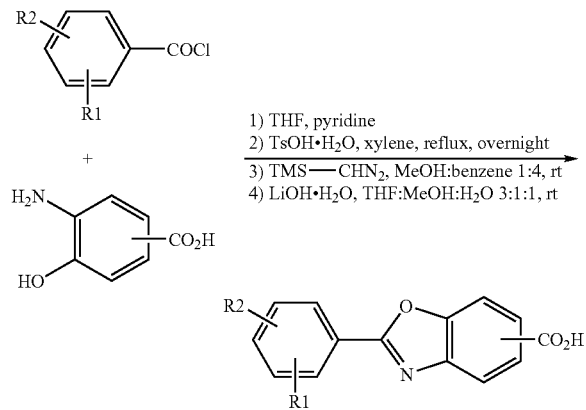

A mixture of amino hydroxybenzoic acid (0.2 mmol) in THF (3 mL) was sequentially treated with pyridine (500 µL, 0.6 mmol) and the desired acid chloride (0.2 mmol). The reaction mixture was stirred at ambient temperature for 10 h, refluxed for 1 h, concentrated in vacuo and used in the next step without purification.

p-Toluenesulfonic acid monohydrate (380.4 mg, 2.0 mmol) was added to the crude reaction mixture in xylenes (5 mL) and the resulting mixture was stirred at reflux overnight. After 12 h, the reaction was cooled to ambient temperature, quenched with NaOH (2 mL, 1 N) and the phases were separated. The aqueous layer was acidified with HCl (1 N) to pH 2 and extracted with EtOAc (4×3 mL). The combined organic layers were dried over MgSO₄, filtered and concentrated in vacuo. (aqueous work up not necessary) The resulting residue was dissolved in a mixture of MeOH:Benzene (2 mL; 1:4), treated with TMS-CHN₂ (200 uL of 2.0 M solution in hexanes, 0.4 mmol) at 25° C. and the reaction progress was monitored by TLC (usually complete after 0.5 h). The reaction mixture was concentrated in vacuo, and the residue was chromatographed (10 to 25% EtOAc/hexanes gradient) to afford the desired benzoxazole methyl ester.

The benzoxazole methyl ester was dissolved in a mixture of THF: MeOH: H₂O (3:1:1, 0.07 M) and treated with LiOH.H₂O (4 equiv). The reaction was stirred at ambient temperature and monitored by TLC. Upon completion, the mixture was acidified to pH 2 with 1 N HCl and extracted with EtOAc (4×). The combined organic layers were dried over MgSO₄, filtered and concentrated. The residue was purified by preparative thin layer chromatography (4.9% MeOH, 95% CH₂Cl₂, 0.1% HOAc) to give the product as a white solid.

Alternate Route:

Reaction was carried out in xylenes with azeotropic removal of water. After the aqueous work up, the precipitated solid is filtered and dissolved in ethyl acetate and diluted with hexane and stirred for 30 min, then filtered off the material precipitated and concentrated the filtrate to 10 ml and filtered the solid precipitated to get pure compound as cream color solid.

E. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with transthyretin (TTR) misfolding, or in which TTR misfolding is implicated, in a pharmaceutically acceptable carrier. Diseases or disorders associated with TTR misfolding include, but are not limited to, familial amyloid polyneuropathy, familial amyloid cardiomyopathy, senile systemic amyloidosis, Alzheimer's disease, spongiform encephalopathy (Creutzfeldt Jakob disease), polyneuropathy, type II diabetes, medullary carcinoma of the thyroid and obesity. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with TTR misfolding or in which TTR misfolding is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with TTR misfolding or in which TTR misfolding is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENâ 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and buccal and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating TTR folding, or for treatment, prevention or amelioration of one or more symptoms of TTR mediated diseases or disorders, or diseases or disorders in which TTR misfolding, is implicated, within the packaging material, and a label that indicates that the compound or composition, or pharmaceutically acceptable derivative thereof, is used for modulating TTR folding, or for treatment, prevention or amelioration of one or more symptoms of TTR mediated diseases or disorders, or diseases or disorders in which TTR misfolding is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which TTR misfolding is implicated as a mediator or contributor to the symptoms or cause.

F. Evaluation of the Activity of the Compounds

A number of in vitro tests can be used to evaluate the compounds for their ability to stabilize transthyretin tetramers or prevent formation of fibrils. The tests can include a fibril formation assay, a plasma selectivity assay, determination of the three-dimensional structure of a transthyretin:compound complex (e.g., by X-ray crystallography), kinetics of transthyretin tetramer dissociation or fibril formations, and determining the stoichiometry and energetics of transthyretin:compound interactions, by, for example, centrifugation or calorimetry. Details of exemplary in vitro assays are presented in the Examples.

The transthyretin used in the screening methods can be wild type transthyretin or a mutant transthyretin, such as a naturally occurring mutant transthyretin causally associated with the incidence of a transthyretin amyloid disease such as familial amyloid polyneuropathy or familial amyloid cardiomyopathy. Exemplary naturally occurring mutant transthyretins include, but are not limited to, V122I, V30M, L55P (the mutant nomenclature describes the substitution at a recited amino acid position, relative to the wild type; see, e.g., Saraiva et al. (2001) *Hum. Mut.* 17:493-503).

For a compound to be an effective drug against TTR amyloidosis, it has to bind to TTR strongly and selectively, so that in blood plasma it partitions into TTR in the presence of all of the other plasma proteins. Therefore, two assays were used to evaluate the compounds. The first assay was a stagnant fibril formation assay that we have described in depth previously. In this assay, a test compound is added at 3.6 or 7.2 µM to a solution of TTR at 3.6 µM. At these two concentrations there is enough test compound to load either one or both of TTR's binding sites. The solution is then placed under amyloidogenic conditions by lowering the pH to 4.4 (the pH at which the rate of TTR amyloid formation is maximal). After 72 h, the turbidity of the TTR solutions (which is related to the extent of TTR aggregation) with the test compounds ($T_{test}$) is measured and compared to that of a solution that lacks any test compound ($T_{control}$). The extent of inhibition of fibril formation is calculated from the differences in turbidity with and without the test compound as:

Inhibition=$(T_{control}-T_{test})/(T_{control})\times 100\%$

High inhibition values indicate very active compounds.

The second assay was an antibody capture method recently developed by this laboratory to measure the test compounds' abilities to bind to TTR in human blood plasma in the presence of all of the other plasma proteins. In this assay the test compound is dissolved to 10.8 µM in human blood plasma (about 3 times the concentration of TTR) and incubated for 24 h. The TTR and any bound small molecule is then immunoprecipitated using a polyclonal TTR antibody bound to sepharose resin. After washing the resin, the antibody-TTR complex is dissociated at high pH and the stoichiometry of TTR to test compound is determined from their peak areas in an HPLC.

High activity in terms of the first assay can be defined as >90% inhibition at 7.2 µM and >60% inhibition at 3.6 µM. In terms of the second assay it can be defined as >1 equiv of test compound bound per equiv of TTR tetramer.

G. Methods of Use of the Compounds and Compositions

Also provided are methods for the stabilization of transthyretin in a tissue or in a biological fluid, and thereby inhibiting misfolding. Generally, the method involves administering to the tissue or biological fluid a stabilizing amount of a compound provided herein that binds to transthyretin and prevents dissociation of the transthyretin tetramer by kinetic stabilization of the native state of the transthyretin tetramer.

Thus, methods which stabilize transthyretin in a diseased tissue ameliorate misfolding and lessen symptoms of an associated disease and, depending upon the disease, can contribute to cure of the disease. Also contemplated herein is inhibition of transthyretin misfolding in a tissue and/or within a cell. The extent of misfolding, and therefore the extent of inhibition achieved by the present methods, can be evaluated by a variety of methods, such as are described in the Examples and in international patent application publication no. WO2004/056315. The disclosure of the above-referenced application is incorporated herein by reference in its entirety.

Also provided herein is a method of treating, preventing, or ameliorating one or more symptoms of a transthyretin amyloid disease, the method involving administering a therapeutically effective amount of a compound provided herein. In one embodiment, the compound prevents dissociation of a transthyretin tetramer by kinetic stabilization of the native state of the transthyretin tetramer. The transthyretin amyloid disease can be, for example, familial amyloid polyneuropathy, familial amyloid cardiomyopathy, or senile systemic amyloidosis. Other transthyretin amyloid diseases include but are not limited to Alzheimer's disease, spongiform encephalopathy (Creutzfeldt Jakob disease), polyneuropathy, type II diabetes and medullary carcinoma of the thyroid (see, e.g., International Patent Application Publication Nos. WO 98/27972 and WO 95/12815).

Methods of treating, preventing, or ameliorating one or more symptoms of a transthyretin mediated disease or disorder by administering a compound provided herein are provided. Transthyretin mediated diseases and disorders include but are not limited to obesity (see, e.g., International Patent Application Publication No. WO 02/059621).

Further provided is a method of stabilizing TTR tetramers using a compound or composition provided herein. Also provided is a method of inhibiting formation of TTR amyloid using a compound or composition provided herein.

Also provided herein is use of any of the compounds or pharmaceutical compositions described herein for the treatment, prevention, or amelioration of one or more symptoms of a transthyretin amyloid disease (e.g., familial amyloid polyneuropathy, familial amyloid cardiomyopathy, or senile systemic amyloidosis).

Also provided herein is use of any of the compounds or pharmaceutical compositions described herein in the manufacture of a medicament for the treatment, prevention, or amelioration of one or more symptoms of a transthyretin amyloid disease (e.g., familial amyloid polyneuropathy, familial amyloid cardiomyopathy, or senile systemic amyloidosis).

H. Combination Therapy

The compounds and compositions provided herein may be administered as a monotherapy or in combination with other active ingredients. For example, the compounds and compositions may be administered in combination with other compounds known for the treatment of amyloidoses and amyloid disorders, including but not limited to, those disclosed in International Patent Application Publication Nos. WO 98/27972, WO 02/059621 and WO 95/12815, and WO2004/056315. Further active ingredients for combination therapy include but are not limited to ARICEPT® and other products approved for treatment of amyloidoses, including but not limited to familial amyloid polyneuropathy, familial amyloid cardiomyopathy, or senile systemic amyloidosis, Alzheimer's disease, spongiform encephalopathy (Creutzfeldt Jakob disease), polyneuropathy, type II diabetes and medullary carcinoma of the thyroid. Further active ingredients for combination therapy include but are not limited to products approved for treatment of obesity.

The following examples are provided for illustrative purposes only and are not intended to limit the scope of the invention.

EXAMPLE 1

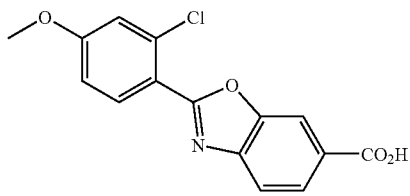

Step 1:

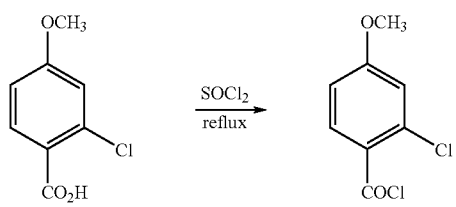

SOCl$_2$ (15 ml) was added to the 2-chloro-4-methoxybenzoic acid (0.285 gm) and refluxed it for 3 hour at 90 degree C. under stirring condition Evaporation of the reaction mixture under vacuum and placed it for further reaction.

Yield (crude)—0.313 gm.

Step 2:

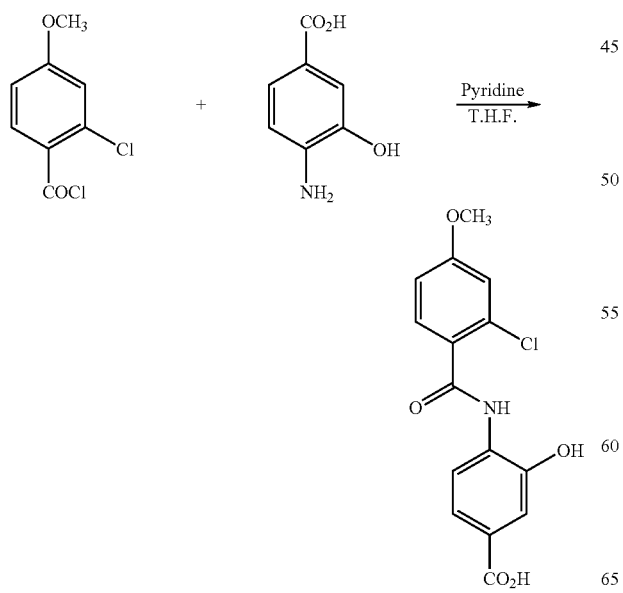

A mixture of 4-amino-3-hydroxybenzoic acid (0.234 gm), T.H.F (15 ml) and Pyridine (0.37 ml) was added to the crude acid chloride (0.313 gm) and refluxed it at 80° C. for overnight. The reaction mixture was poured into water and then extracted in diethyl ether and on evaporation gave the amide.

Yield—0.8 gm.

Step 3:

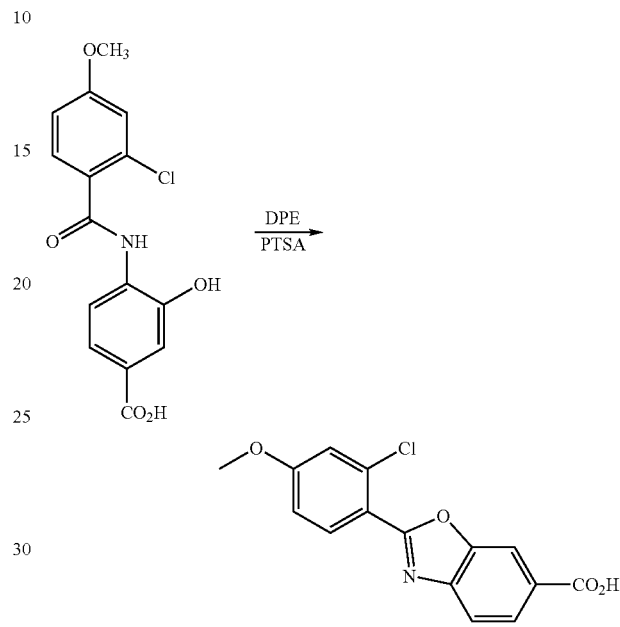

The acid amide (0.8 gm) was dissolved in Diphenyl ether (25 ml) and PTSA (68 mg) was added to it, and kept for overnight under refluxing condition at 220° C. On completion of the reaction the product was collected by filtration and washed with hexane and diethyl ether.

Yield—0.405 gm

Step 4:

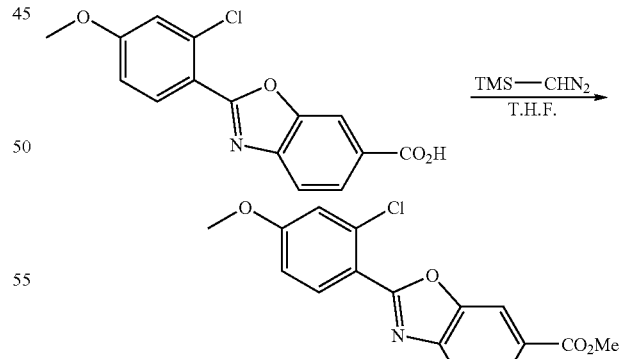

The acid (0.405 gm) was dissolved in 15 ml T.H.F and 0.424 ml of T.M.S—CHN$_2$ was added to the solution and kept it for overnight under stirring condition. The reaction mixture was purified by flash chromatography by 5% hexane ethyl acetate solution.

Yield—0.107 gm.

Step 5:

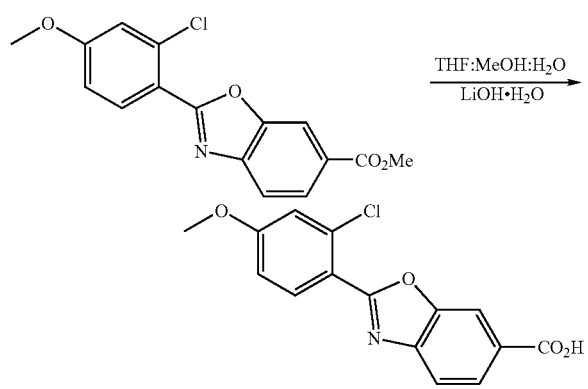

The methyl ester (0.090 gm) was dissolved in 10 ml of T.H.F:MeOH:H₂O (3:1:1) and LiOH.H₂O (0.048 gm) was added to it and stirred for 4 hour. On completion the reaction mixture was diluted and acidified by 1N HCl, extracted in ethyl acetate, washed with brine solution and conc. in vacuum. Pale yellowish solid was found.

| Yield | .084 gm. |
| --- | --- |
| % of Yield | 97.67%. |
| Final compound | |
| Color | Pale yellowish. |
| State | Solid. |
| Weight | 84 mg. |

EXAMPLE 2

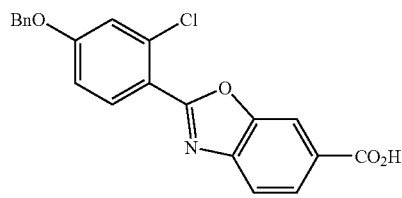

Step One:

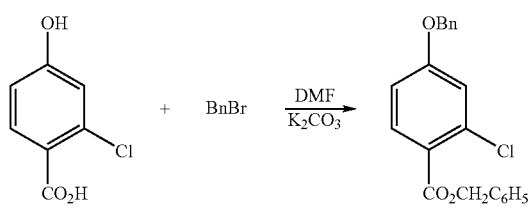

2-Chloro-4-hydroxy benzoic acid (0.5 gram) was dissolved in DMF (10 ml), K₂CO₃ (1.201 gram) was added to it and then stirred by adding Benzyl bromide (0.688 ml) (drop wise) under 0 degree C., and kept it for 1 hour. After completing the reaction water was added and extracted by ethylacetate, washed with brine soln, dried by sodiumsulphate and conc. bye vacuum. After that it was purified by flash chromatography, eluting with hexane. Ethyl acetate solution (5%).

Yield—0.930 gram.

Step Two:

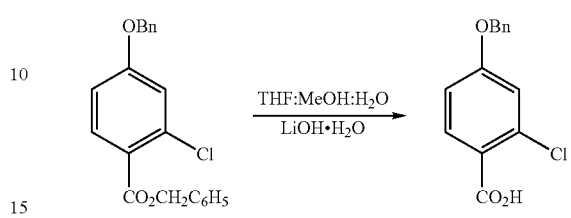

The dibenzyl ester (0.5 gram) was dissolved in THF:MeOH:H₂O (3:1:1), 10 ml and LiOH.H₂O (0.24 gram) was added to it and stirred for 4 hours at room temp., on completion the reaction mixture was diluted with water and acidified by 1 N HCl, extracted in ethyl acetate, washed with brine solution and concentrated in vaccum to give a pale yellowish solid Yield—0.157 gram.

Step Three:

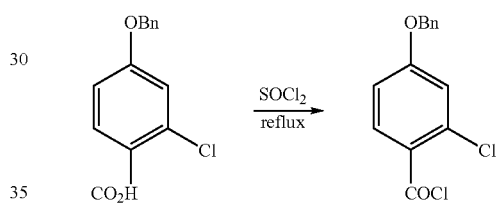

Thionyl chloride was added to the acid followed by a drop of DMF and stirred under reflux condition at 80 degree C. for 4 hour. Evaporation of the reaction under vacuum and the crude acid chloride was used for further reaction.

Step Four:

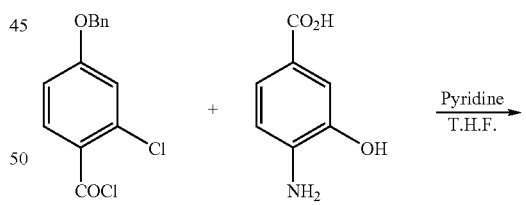

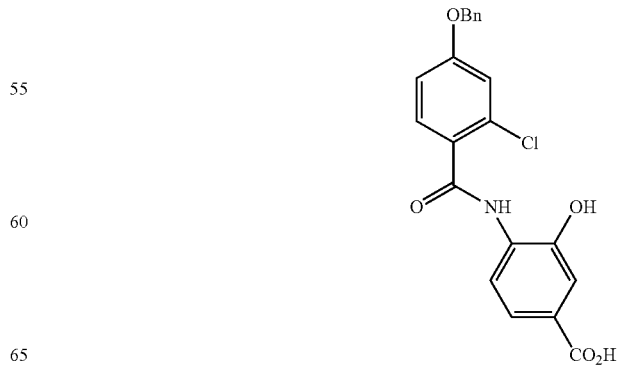

A solution of 4-amino-3-hydoxy benzoic acid (0.122 gram) in THF (15 ml) was sequentially treated with Pyridine (0.19 ml). Acid chloride was dissolved in THF and added to the mixture drop by drop at 0 degree C. and then stirred for overnight at room temp., evaporated in vacuum, the crude one was used for the further reaction.

Yield—0.485 gram.

Step Five:

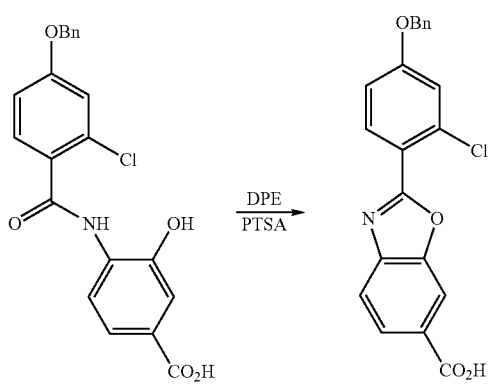

The acid amide (0.485 gram) was dissolved in DPE and PTSA (10 mole %) was added to it and refluxed for 3 hour at 200-220 degree C. The solid was obtained consisted a mixture of desired as well as side product.

Yield—0.430 gram.

Step Six:

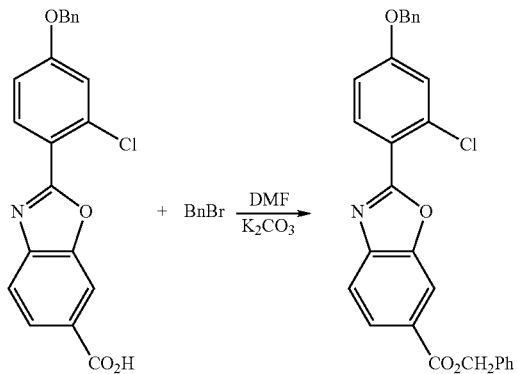

The acid (0.430 gram) was dissolved in DMF (20 ml), $K_2CO_3$ (0.57 gram) was added to it and then stirred by adding Benzyl bromide (0.35 ml) drop by drop under 0 degree C. and kept it for 1 hour. after completing the reaction water was added and extracted by ethyl acetate, washed with brine solution, dried by sodium sulphate and conc. in vacuum. After that the crude was purified by flash chromatography by using 7% Hexane ethyl acetate solution.

Yield—0.469 gram.

Step Seven:

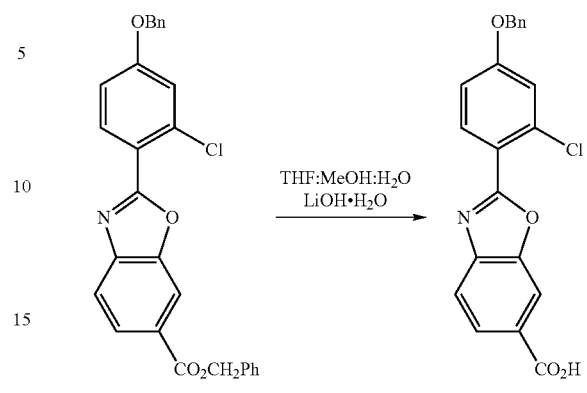

The dibenzyl ester (0.170 gram) was dissolved in THF:MeOH:$H_2O$ (3:1:1) and LiOH.$H_2O$ (0.061 gram) was added to it and stirred for 4 hour at room temp. On completing the reaction mixture was diluted with water and acidified by 1 N HCl, extracted by ethyl acetate, washed with brine solution and concentrated in vacuum. It was washed with ethyl acetate and as a result white solid was found.

| Yield | .044 mg. |
|---|---|
| Final compound: | |
| Colour | White. |
| Melting Point | 226.2 degree C. |
| Weight | 43 mg. . . . |

EXAMPLE 3

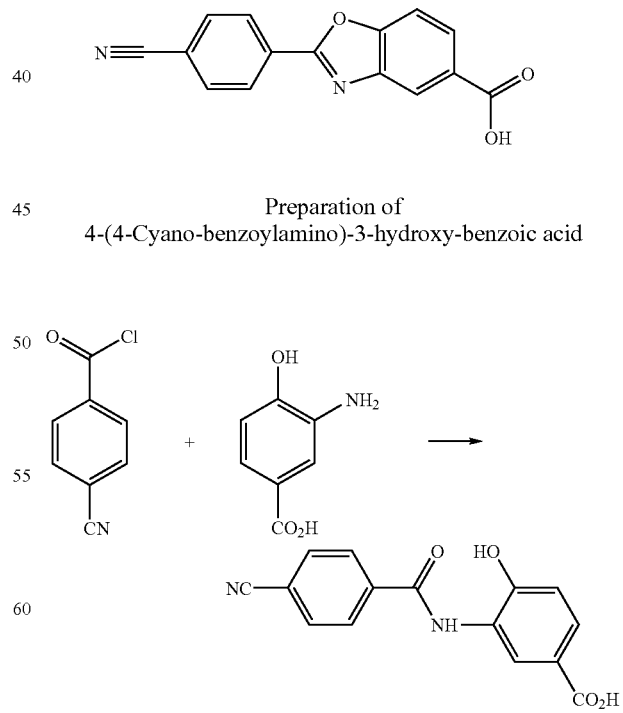

Preparation of 4-(4-Cyano-benzoylamino)-3-hydroxy-benzoic acid

To a stirred solution of 3-Amino-4-hydroxy benzoic acid (0.185 g, 0.0012 mols) and pyridine (0.287 g, 0.00363 mols)

in 18.5 ml dry THF is added 4-cyanobenzoyl chloride (0.2 g, 0.0012 mols) and the solution is stirred under nitrogen atmosphere at RT for 10 hrs and then refluxed for 3 hrs. The reaction mixture is rotary evaporated and the residue is slurried in water and filtered to get the amide (0.18 g) which is taken for the next step without further purification.

Preparation of 2-(4-Cyano-phenyl)-benzooxazole-5-carboxylic acid

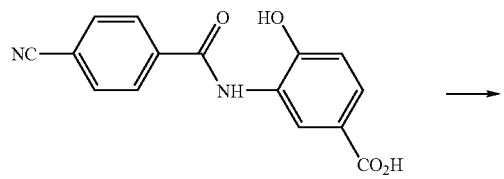

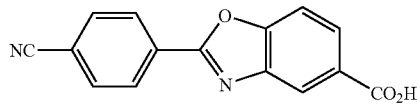

The above amide is suspended in 30 ml Xylene in a single necked RB flask fitted with a DEAN-STARCK apparatus and 40 mg of p-Toluenesulfonic acid is added. The Reaction mixture is then refluxed at 160° C. for 12 hrs. The RM upon cooling is filtered. The residue is slurried in Diethyl ether and again filtered. The residue is then stirred in 1.5N HCl for 30 mins and extracted in Ethyl acetate, dried over anhydrous sodium sulfate and rotary evaporated to get 0.045 g of the pure title compound.

EXAMPLE 4

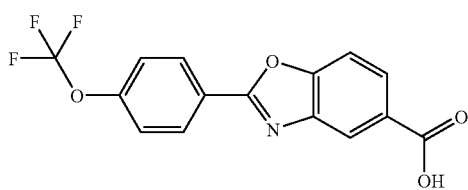

Preparation of 4-Hydroxy-3-(4-trifluoromethoxy-benzoylamino)-benzoic acid

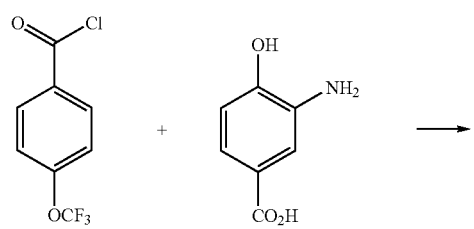

-continued

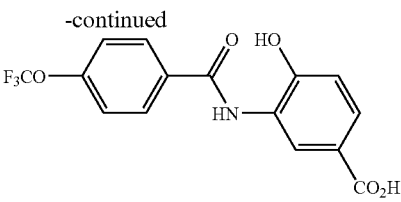

To a stirred solution of 3-Amino-4-hydroxy benzoic acid (0.136, 0.00089 mols) and pyridine (0.211 g, 0.00267 mols) in 13 ml dry THF is added 4-trifluoromethoxybenzoyl chloride (0.2 g, 0.00089 mols) and the solution is stirred under nitrogen atmosphere at RT for 10 hrs and then refluxed for 3 hrs. The reaction mixture is rotary evaporated and the residue is slurried in water and filtered to get the amide (0.175 g) which is taken for the next step without further purification.

Preparation of 2-(4-Trifluoromethoxy-phenyl)-benzooxazole-5-carboxylic acid

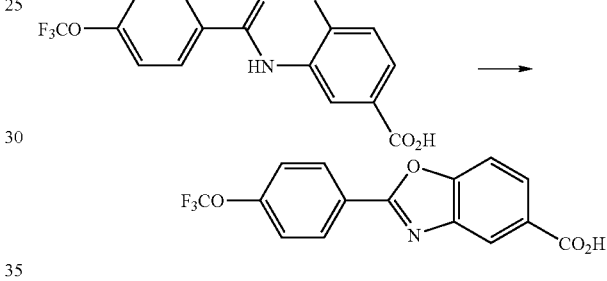

The above amide is suspended in 30 ml Xylene in a single necked RB flask fitted with a DEAN-STARCK apparatus and 40 mg of p-Toluenesulfonic acid is added. The Reaction mixture is then refluxed at 160° C. for 12 hrs. The RM upon cooling is filtered. The residue is slurried in Diethyl ether and filtered to get the pure title compound (70 mg).

EXAMPLE 5

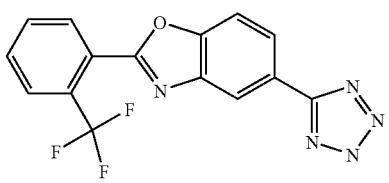

Step 1

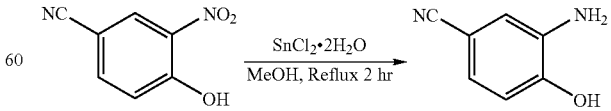

Nitro compound was dissolved in methanol and added $SnCl_2.2H_2O$, heated to reflux. reaction completed in 2 hr. Concentrated solvent completely, added cold water, washed with ethyl acetate. Aqueous layer basified with bicarbontate solution and extracted with ethylacetate. Organic layer washed with D.M. water and brine solution respectievely. Dried on Na₂SO₄ and concentrated.
Nature: solid
Yield: 82.8%
Purity: 91.64%
Step 2

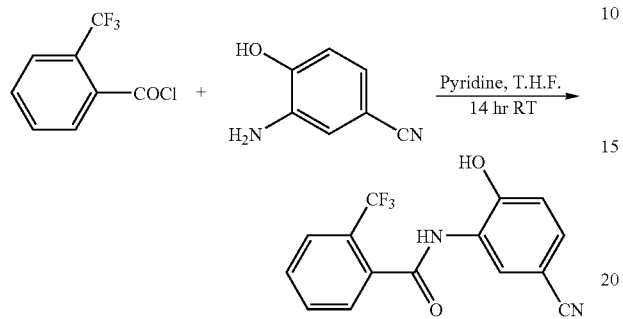

Aminohydroxybenzonitrile (Step 1) in THF was sequentially treated with pyridine and acid chloride. The reaction mixture was stirred at RT for 14 hr, concentrated in vaccuo and used in the next step with out purification.
Step 3

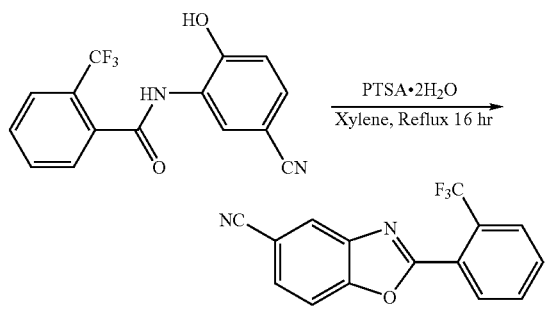

PTSA.H₂O was added to the crude amide (Step 2) in xylene and resulting mixture was stirred at reflux overnight. After 16 hr, cooled to rt and concentrated in vacuo. The residue was chromatographed (5 to 10c/o EtOAc/Hexane) to afford the desired cyclised cyano product.
Nature: white solid
% Yeild: 53%
Purity: 100%
Step 4

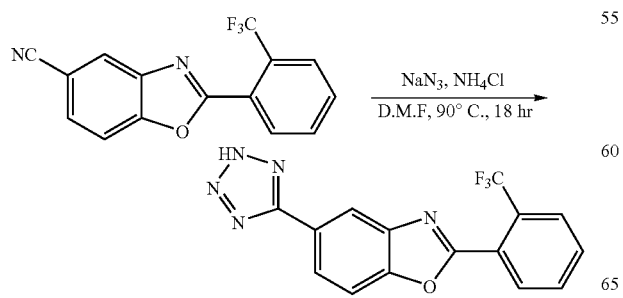

Benzonitrile (Step 3) compound and NH₄Cl taken in DMF. The mixture was cooled to 0° C., and NaN₃ was added portion wise over 5-6 min. The reaction mixture was stirred at 0° C. for 5 min and at RT 15 min. The reaction mixture was heated at 40° C. for 1 h and then slowly increased to 90° C. over a period of 3 h. The reaction mixture was stirred at 90° C. for 20 h and then cooled to 0-5° C. The reaction was quenched with water and ₚH adjusted to 2 with 1N HCl, extracted with EtOAc. The combined organic layer were washed with water, dried and concentrated to give a gum, which was thoroughly dried under vacuum for 2 h to affored light brown solid. The solid washed with 5% hexane:EtAc mixture and dried.
Nature: Pale brown solid
Yield: 60.9%
Purity: 99.8%

EXAMPLE 6

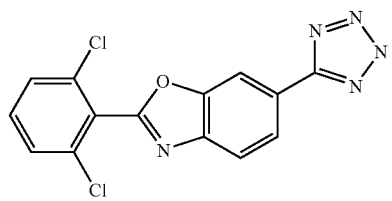

Step 1

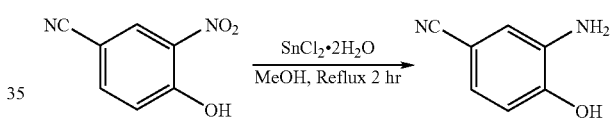

Nitro compound was dissolved in methanol and added SnCl₂.2H₂O, heated to reflux.reaction completed in 2 hr. Concentrated solvent completely, added cold water, washed with ethyl acetate.aqous layer basified with bicarbontate solution and extracted with ethylacetate.organic layer washed with D.M. water and brine solution respectievely. Dried on Na₂SO₄ and concentrated.
Nature: solid
% Yeild: 82.8%
Purity: 91.64%
Step 2

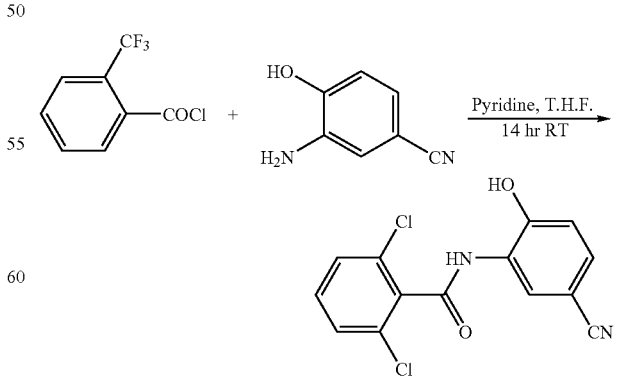

Aminohydroxybenzonitrile in THF was sequentially treated with pyridine and desired acid chloride. The reaction mixture was stirred at RT for 14 hr, concentrated in vacuo and added ethylacetate, washed with 1% HCl and brine. Dried on Na$_2$SO$_4$ and concentrated.
Nature: Solid
% Yeild: 66%
Purity: 88.9%
Step 3

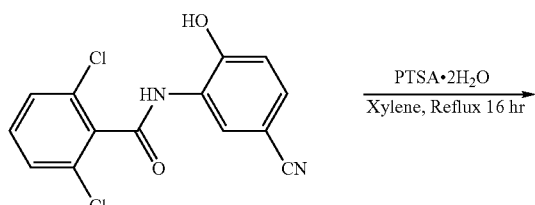

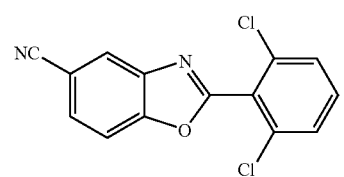

PTSA.H$_2$O was added to the crude reaction mixture in xylene and resulting mixture was stirred at reflux overnight. After 16 hr, cooled to rt and concentrated in vacuo. The residue was chromatographed (5 to 10c/o EtOAc/Hexane) to afford the desired cyclised cyano product.
Nature: white solid
% Yield: 30.4%
Purity: 97.2%
Step 4

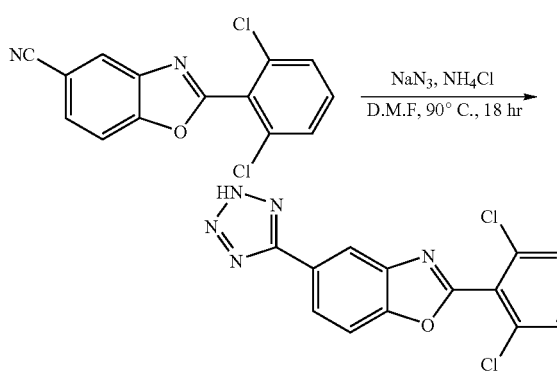

Benzonitrile compound and NH$_4$Cl taken in DMF. The mixture was cooled to 0° C., and NaN$_3$ was added portionwise over 5-6 min. The reaction mixture was stirred at 0° C. for 5 min and at RT 15 min. The reaction mixture was heated at 40° C. for 1 h and then slowly increased to 90° C. over a period of 3 h. The reaction mixture was stirred at 90° C. for 20 h and then cooled to 0-5° C. The reaction was quenched with water and $_p$H adjusted 2 with 1N HCl, and extracted with EtOAc. The combined organic layer were washed with water, dried and concentrated to give a gum, which was thoroughly dried under vacuum for 2 h to affored light brown solid. The solid washed with 5% hexane:EtAc mixture and dried.
Nature: Pale brown solid
% Yield: 48%
Purity: 99.8%

EXAMPLE 7

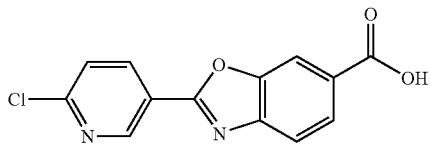

Preparation of 4-[(6-Chloro-pyridine-3-carbonyl)-amino]-3-hydroxy-benzoic acid

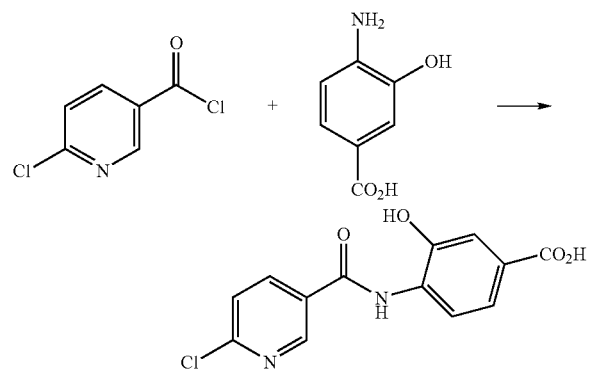

To a stirred solution of 4-Amino-3-hydroxy benzoic acid (0.490 g, 0.0032 mols) and pyridine (0.76 g, 0.0096 mols) in 50 ml dry THF is added 6-chloronicotinoyl chloride (0.56 g, 0.0032 mols) and the solution is stirred under nitrogen atmosphere at RT for 10 hrs and then refluxed for 3 hrs. The reaction mixture is rotary evaporated and the residue is slurried in water and filtered to get the amide (0.8 g) which is taken for the next step without further purification.

Preparation of 2-(6-Chloro-pyridin-3-yl)-benzooxazole-6-carboxylic acid

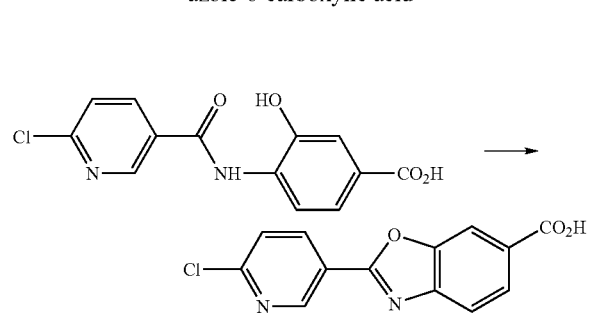

The above amide is suspended in 75 ml Xylene in a single necked RBflask fitted with a DEAN-STARCK apparatus and 150 mg of p-Toluenesulfonic acid is added. The Reaction mixture is then heated up to 160° C. gradually over a period of 5 hrs and then held at that temperature for 12 hrs. The reaction mixture upon cooling is filtered. The residue is slurried in Diethyl ether and filtered to get the crude product which is purified by preparative HPLC to get the pure title compound.

0.2 g of crude compound yields 0.55 g of the pure product.

EXAMPLE 8

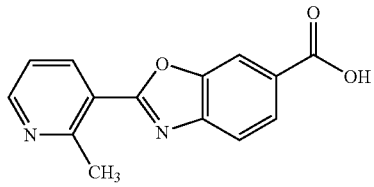

Preparation of 3-Hydroxy-4-[(2-methyl-pyridine-3-carbonyl)-amino]-benzoic acid

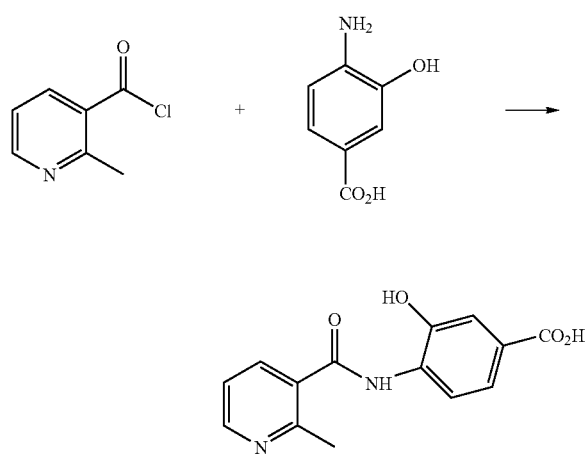

2-methyl nicotinoyl chloride (0.2 g, 0.00128 mols) is dissolved in 30 ml dry DCM and N,N'-Diisopropylethylamine (0.994 g, 0.00769 mols) is added slowly to the acid chloride solution at 0° C. under nitrogen atmosphere. A solution of 4-Amino-3-hydroxybenzoic acid (0.196 g, 0.00128 mols) in 10 ml dry THF is slowly added to the above solution at 0° C. The solution is then stirred at 0° C. for 30 mins and then at RT overnight. The reaction mixture is then diluted with 100 ml Ethyl acetate and stirred for 30 mins. The precipitated tarry material is filtered off over celite bed and the organic phase given 4×20 ml water wash, 2×10 ml brine wash dried over sodium sulfate and rotary evaporated to get the crude amide (140 mg) which is taken for the cyclisation step without further purification.

Preparation of 2-(2-Methyl-pyridin-3-yl)-benzooxazole-6-carboxylic acid

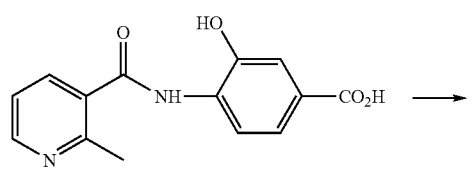

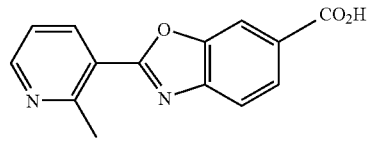

The crude amide is dissolved in 10 ml DMSO and 40 mg p-Toluenesulfonic acid is added. The solution is then subjected to microwave irradiation with short bursts for 15 mins. The reaction mixture is then allowed to cool to RT and then poured into ice-cold water with stirring. The aqueous phase is then extracted with 4×50 ml Ethyl acetate. The organic phase is given 2×20 ml water wash, brine wash dried over sodium sulfate and rotary evaporated to get the crude product (100 mg) which is purified by preparative HPLC.

200 mg of the crude 2-(2-Methyl-pyridin-3-yl)-benzooxazole-6-carboxylic acid upon purification by preparative HPLC yielded 20 mg of the pure product.

EXAMPLE 9

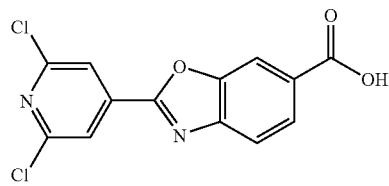

Preparation of 4-[(2,6-Dichloro-pyridine-4-carbonyl)-amino]-3-hydroxy-benzoic acid

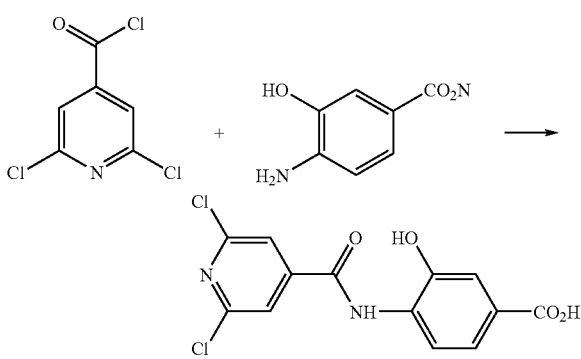

2-methyl nicotinoyl chloride (0.2 g, 0.00128 mols) is dissolved in 30 ml dry DCM and N,N'-Diisopropylethylamine (0.994 g, 0.00769 mols) is added slowly to the acid chloride solution at 0° C. under nitrogen atmosphere. A solution of 4-Amino-3-hydroxybenzoic acid (0.196 g, 0.00128 mols) in 10 ml dry THF is slowly added to the above solution at 0° C. The solution is then stirred at 0° C. for 30 mins and then at RT overnight. The reaction mixture is then diluted with 100 ml Ethyl acetate and stirred for 30 mins. The precipitated tarry material is filtered off over celite bed and the organic phase given 4×20 ml water wash, 2×10 ml brine wash dried over sodium sulfate and rotary evaporated to get the crude amide (140 mg) which is taken for the cyclisation step without further purification.

Preparation of 2-(2,6-Dichloro-pyridin-4-yl)-benzooxazole-6-carboxylic acid

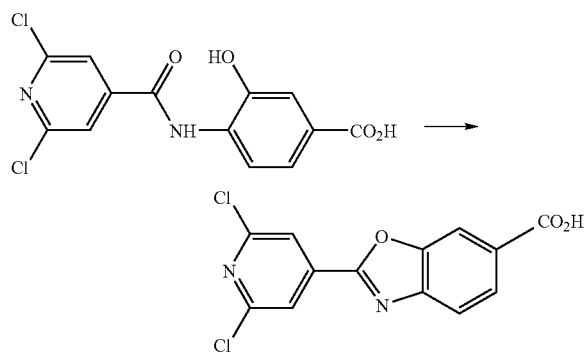

the above amide is suspended in 25 ml Xylene in a single necked RBflask fitted with a DEAN-STARCK apparatus and 40 mg of p-Toluenesulfonic acid is added. The Reaction mixture is then heated up to 160° C. gradually over a period of 5 hrs and then held at that temperature for 12 hrs. The RM upon cooling is filtered. The residue is slurried in Diethyl ether and filtered to get 0.65 g of the pure product.

Other compounds provided herein have been prepared by minor modification of the above Examples that are within the knowledge of one of skill in the art. These compounds are shown below, along with observed melting points.

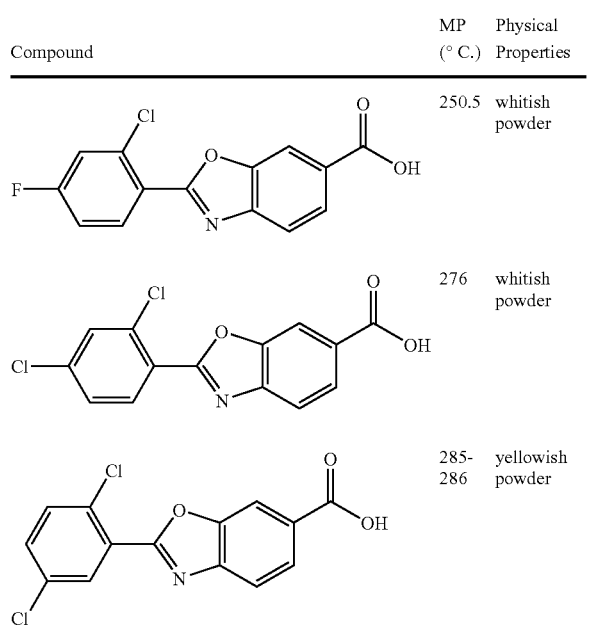

| Compound | MP (° C.) | Physical Properties |
|---|---|---|
| | 250.5 | whitish powder |
| | 276 | whitish powder |
| | 285-286 | yellowish powder |
| | 204 | whitish powder |
| | 285 | whitish powder |
| | ND | beige powder |
| | ND | whitish powder |
| | ND | white powder |
| | 265-266 | — |
| | 246 (dec) | — |
| | 245 (dec) | — |

EXAMPLE 10

The compounds provided herein were subjected to a stagnant fibril formation assay. Compounds were dried over $P_2O_5$ overnight and dissolved in DMSO to a final concentration of 7.2 mM to provide a primary stock solution (10× stock). A secondary stock solution was prepared by five-fold dilution of the primary stock solution with DMSO to a final concentration of 1.44 mM (2× stock). The acid-mediated amyloidogenicity of TTR (3.6 μM) in the presence of inhibitors (1.44 mM) was measured as follows: To a disposable UV cuvette were added 495 μL of a 0.4 mg/mL WT TTR protein solution in 10 mM sodium phosphate, 100 mM KCl and 1 mM EDTA (pH 7.6) and 5 μL of the 1.44 mM secondary stock inhibitor solution in DMSO (2× stock). The mixture was vortexed and incubated for 30 min (25° C.), at which time the pH was lowered to 4.4 with 500 μL of 200 mM acetate, 100 mM KCl and 1 mM EDTA (pH 4.2). The final 1 mL solution was vortexed and incubated for 72 h at 37° C. without agitation. After 72 h, the cuvettes were vortexed to suspend any fibrils present, and the turbidity of the suspension was measured at 350 and 400 nm using a UV-vis spectrometer. The percent fibril formation was obtained by the ratio of the observed turbidities for each TTR plus inhibitor sample relative to that of a sample prepared the same way, but lacking inhibitor, multiplied by 100. The fibril formation assay employing equimolar inhibitor and TTR concentrations (3.6 μM) was performed as above using a 1× secondary stock solution. The 1× stock solution was prepared by ten-fold dilution of the 7.2 mM 10× primary stock solution with DMSO to a final concentration of 0.72 mM and used in the fibril formation assay as described above. All assays were performed in triplicate and all compounds were assayed using wild-type TTR. All compounds were found to be soluble throughout the course of the experiment by testing the turbidities of the solutions in the absence of WT TTR, ensuring that turbidity was the result of TTR amyloid formation.

The binding stoichiometries of potential inhibitors to TTR in blood plasma were evaluated by an antibody capture/HPLC method. A 1.5-mL eppendorf tube was filled with 1.0 mL of human blood plasma and 7.5 μL of a 1.44 mM DMSO solution of the inhibitor under evaluation. The solution was incubated and gently rocked at 37° C. for 24 h. A 1:1 gel:TSA (Tris saline) slurry (125 μL) of quenched sepharose was added to the solution and gently rocked at 4° C. for 1 h. The solution was centrifuged (16,000×g) and the supernatant was divided into two 400 μL aliquots, which were then added to different 200 μL samples of a 1:1 gel:TSA slurry of the anti-TTR antibody-conjugated sepharose. The solutions were gently rocked at 4° C. for 20 min, centrifuged (16,000×g), and the supernatant was removed. The gel was washed with 1 mL of TSA/0.05% saponin (3×, 10 min each) at 4° C., followed by 1 mL of TSA (2×, 10 min each) at 4° C. The samples were centrifuged (16,000×g), the final wash was removed, and 155 μL of 100 mM triethylamine, pH 11.5, was added to elute the TTR and bound inhibitors from the antibodies. After gentle rocking at 4° C. for 30 min, the elution sample was centrifuged (16,000×g) and 145 μL of the supernatant, containing TTR and inhibitor, were removed. The supernatant was then analyzed by reverse-phase HPLC as described previously. See, for example, Purkey, H. E.; Dorrell, M. I.; Kelly, J. W. *Proc. Natl. Acad. Sci. U.S.A.* 2001, 98, 5566-71, which is incorporated by reference in its entirety.

The kinetics of TTR tetramer dissociation was evaluated by linked monomer unfolding in urea. Slow tetramer dissociation is not detectable by far-UV CD spectroscopy, but is linked to the rapid (500,000-fold faster) unfolding step easily detectable by far-UV CD as described previously. TTR tetramer (3.6 μM) dissociation kinetics as a function of inhibitor (3.6 μM) were evaluated by adding 3.6 μL of a 1 mM solution (in ethanol) of the inhibitor of interest to 69 μL of WT TTR (2.90 mg/mL, 10 mM sodium phosphate, 100 mM KCl, 1 mM EDTA, pH 7.0) to which was added 127.4 μL of phosphate buffer. For an inhibitor concentration (7.2 μM) twice that of the TTR concentration (3.6 μM), 7.2 μL of a 1 mM solution (in ethanol) of the inhibitor of interest was added to 69 μL of WT TTR (2.90 mg/mL, 10 mM sodium phosphate, 100 mM KCl, 1 mM EDTA, pH 7.0) to which was added 123.8 μL of phosphate buffer. 100 μL of the protein-inhibitor solution of interest was added to a solution of 600 μL of 10.3 M urea and 300 μL of phosphate buffer, to yield a final urea concentration of 6.5 M. The solutions were vortexed and the circular dichroism spectra were collected at the following intervals: 0, 5, 8, 23, 46, 71, 95, 118, 144 and 168 h. A control sample containing 7.2 μL of ethanol rather than inhibitor was prepared for comparison and the spectra were collected at the time points identified above. CD spectra were collected between 220 and 213 nm, with scanning every 0.5 nm and an averaging time of 10 sec. Each wavelength was scanned once. The values for the amplitude were averaged between 220 and 213 nm to determine the extent of β-sheet loss throughout the experiment.

The rate of acid-mediated fibril formation was followed at pH 4.4 by turbidity. Compounds were dried over $P_2O_5$ overnight and dissolved in DMSO to a final concentration of 7.2 mM to provide a primary stock solution (10× stock). A secondary stock solution was prepared by five-fold DMSO dilution of the primary stock solution to yield a final concentration of 1.44 mM (2× stock). The fibril formation assay employing an inhibitor concentration of 7.2 μM relative to 3.6 μM TTR (tetramer) was performed as follows: To a disposable UV cuvette were added 495 μL of a 0.4 mg/mL WT TTR protein solution in 10 mM sodium phosphate, 100 mM KCl and 1 mM EDTA (pH 7.6) and 5 μL of the 1.44 mM secondary inhibitor stock solution (2× stock). The mixture was vortexed and incubated for 30 min (25° C.). After 30 min, the pH was lowered to 4.4 with 500 μL of 200 mM acetate, 100 mM KCl, 1 mM EDTA (pH 4.2). The final 1 mL solution was vortexed and incubated at 37° C. without agitation. The solutions were vortexed and turbidity at 350 and 400 nm was measured. UV spectra were collected at the following intervals: 0, 4, 8, 24, 48, 72, 96, 120, 144, 168 and 192 h after acidification. A control sample containing 5 μL of DMSO was prepared for comparison, and the spectra were collected at the time points above. Each inhibitor solution was prepared in groups of 10 to prevent disturbance of the cuvettes before a reading was taken. After a UV absorbance was obtained, the cuvettes corresponding to that time-point were discarded. The fibril formation assay employing equimolar (3.6 μM) TTR and inhibitor concentration was performed as above using a 1× secondary inhibitor stock solution prepared as follows: A stock solution was prepared by ten-fold dilution of the 7.2 mM 10× primary stock solution with DMSO to a final concentration of 0.72 mM and used in the fibril formation assay as described above. All compounds were found to be soluble throughout the course of the experiment, ensuring that turbidity was the result of TTR amyloid formation.

The compounds described were evaluated as TTR amyloid fibril inhibitors using a turbidity assay. WT TTR amyloidosis was initiated by acidification of TTR preincubated with inhibitor (25° C., 30 min), employing buffer addition to jump the pH to a final value of 4.4. After incubation of each mixture for 72 h (37° C.), the turbidity was measured at 350 and 400 nm using a UV-vis spectrometer. All amyloid fibril formation data was normalized to WT TTR amyloidogenesis in the absence of inhibitor, assigned to be 100% fibril formation. Therefore, 5% fibril formation corresponds to a compound inhibiting 95% of WT TTR fibril formation after 72 h. Each potential inhibitor was first evaluated at a concentration of 7.2 μM relative to a TTR tetramer concentration of 3.6 μM. Compounds allowing less than 15% fibril formation were reevaluated at a concentration equal to the TTR concentration (3.6 μM) to select for the inhibitors with the highest efficacy. Fibril formation of less than 40% under these conditions is characteristic of a very good inhibitor, whereas 40-70% inhibition is indicative of a modest compound.

Inhibitors that keep TTR fibril formation below 50% at a concentration equal to that of TTR (3.6 µM) were further evaluated for their ability to bind TTR selectively over all other proteins in blood plasma. The diflunisal concentration in blood can exceed 30 µM 20 h after a single 500 mg dose, or 300 µM 4 h after the same dose. While this high level of sustained plasma concentration suggests excellent bioavailability, more selective inhibitors will allow for lower dosing and potentially fewer side-effects; therefore, human plasma was incubated with this subset of inhibitors at a final concentration of 10.8 µM (average TTR concentration in human plasma is approximately 5 µM). TTR was then captured using a resin-bound antibody, and the immobilized TTR was washed three times with a solution of TSA (tris saline)/0.05% saponin, followed by two washes with TSA. The TTR-inhibitor complex was liberated from the resin with 100 mM triethylamine (pH 11.5), and the stoichiometry of inhibitor present relative to TTR was determined by reverse-phase HPLC analysis. A maximum of 2 equiv of inhibitor may be bound per TTR tetramer.

Materials and Methods

Transthyretin Antibody Purification and Conjugation to Sepharose

Antibodies were produced, purified and coupled to Sepharose. The resin was stored as a 1:1 slurry in TSA (10 mM Tris, pH 8.0/140 mM NaCl/0.025% $NaN_3$). In addition, quenched Sepharose was prepared by coupling 200 mM Tris, pH 8.0 to the resin instead of the antibody.

Human Plasma Preparation

Whole blood was drawn from healthy volunteers at the Scripps General Clinical Research Center's Normal Blood-Drawing Program and transferred to 50 mL conical tubes. The tubes were centrifuged at 3000 RPM (1730×g) in a Sorvall RT7 benchtop centrifuge equipped with a swinging bucket rotor for 10 min at 25° C. The plasma supernatant was removed and centrifuged again at 3000 RPM for 10 min to remove the remaining cells. Sodium azide was added to give a 0.05% solution. The plasma was stored at 4° C. until use Immunoprecipitation of Transthyretin and Bound Compounds A 2 mL eppendorf tube was filled with 1.5 mL of human blood plasma and 7.5 µL of a 2.16 mM DMSO solution of the compound under evaluation. This solution was incubated at 37° C. for 24 h. A 1:1 resin/TSA slurry (187 µL) of quenched Sepharose was added to the solution and gently rocked at 4° C. for 1 h. The solution was centrifuged (16,000×g) and the supernatant divided into 3 aliquots of 400 µL each. These were each added to 200 µL of a 1:1 resin/TSA slurry of the anti-transthyretin antibody-conjugated Sepharose and slowly rocked at 4° C. for 20 min. The samples were centrifuged (16,000×g) and the supernatant removed. The resin was washed with 1 mL TSA/0.05% Saponin (Acros) (3×10 min) at 4° C., and additionally with 1 mL TSA (2×10 min) at 4° C. The samples were centrifuged (16,000×g), the final wash removed, and 155 µL of 100 mM triethylamine, pH 11.5 was added to elute the TTR and bound small molecules from the antibodies. Following gentle rocking at 4° C. for 30 min, the samples were centrifuged (16,000×g) and 145 µL of the supernatant, containing TTR and inhibitor, was removed.

HPLC Analysis and Quantification of Transthyretin and Bound Compounds

The supernatant elution samples from the TTR antibody beads (145 µL) were loaded onto a Waters 71P autosampler. A 135 µL injection of each sample was separated on a Keystone 3 cm C18 reverse phase column utilizing a 40-100% B gradient over 8 min (A: 94.8% $H_2O$/5% acetonitrile/0.2% TFA; B: 94.8% acetonitrile/5% $H_2O$/0.2% TFA), controlled by a Waters 600E multisolvent delivery system. Detection was accomplished at 280 nm with a Waters 486 tunable absorbance detector, and the peaks were integrated to give the area of both TTR and the small molecule. In order to determine the quantity of each species, known amounts of tetrameric TTR or compound were injected onto the HPLC. The peaks were integrated to create calibration curves from linear regressions of the data using Kaleidagraph (Synergy Software). The calibration curves were used to determine the number of moles of each species present in the plasma samples. The ratio of small molecule to protein was calculated to yield the stoichiometry of small molecule bound to TTR in plasma.

Transthyretin Amyloid Fibril Formation Assay

The compounds were dissolved in DMSO at a concentration of 720 µM. Five µL of a solution of the compound being evaluated was added to 0.5 mL of a 7.2 µM TTR solution in 10 mM phosphate pH 7.6, 100 mM KCl, 1 mM EDTA buffer, allowing the compound to incubate with TTR for 30 min. 495 µL of 0.2 mM acetate pH 4.2, 100 mM KCl, 1 mM EDTA was added, to yield final protein and inhibitor concentrations of 3.6 µM each and a pH of 4.4. The mixture was then incubated at 37° C. for 72 h, after which the tubes were vortexed for 3 sec and the optical density was measured at 400 nm. The extent of fibril formation was determined by normalizing each optical density by that of TTR without inhibitor, defined to be 100% fibril formation. Control solutions of each compound in the absence of TTR were also tested and none absorbed appreciably at 400 nm.

Crystallization and X-ray Data Collection

Crystals of recombinant TTR were obtained from protein solutions at 5 mg/ml (in 100 mM KCl, 100 mM phosphate, pH 7.4, 1 M ammonium sulfate) equilibrated against 2 M ammonium sulfate in hanging drop experiments. The TTR.ligand complexes were prepared from crystals soaked for 2 weeks with a 10-fold molar excess of the ligand to ensure full saturation of both binding sites. 1:1 acetone:water solution was used as a soaking agent. A DIP2030b imaging plate system (MAC Science, Yokohama, Japan) coupled to a RU200 rotating anode X-ray generator was used for data collection. The crystals were placed in paratone oil as a cryo-protectant and cooled to 120 K for the diffraction experiments. Crystals of all TTR.ligand complexes are isomorphous with the apo crystal form containing unit cell dimensions a=43 Å, b=86 Å and c=65 Å. They belong to the space group $P2_12_12$ and contain half of the homotetramer in the asymmetric unit. Data were reduced with DENZO and SCALEPACK.

Structure Determination and Refinement

The protein atomic coordinates for TTR from the Protein Data Bank (accession number 1BMZ) were used as a starting model for the refinement of native TTR and the TTR-ligand complexes by molecular dynamics and energy minimization using the program CNS. Maps were calculated from diffraction data collected on TTR crystals either soaked with compounds or cocrystalized simultaneously. For the complexes of TTR with the compounds, the resulting maps revealed approximate positions of the ligand in both binding pockets of the TTR tetramer, with peak heights of above 5-9 r.m.s. In order to further improve the small molecule electron density and remove the model bias, the model was subjected to several cycles of the warp/shake protocol, which resulted in noticeable improvement in the map, especially around the inhibitor. Subsequent model fitting was done using these maps and the ligand molecule was placed into the density. In all three cases the minimum-energy conformation of the inhibitor calculated by the program InsightII (Accelrys) was in good agreement with the map. Because of the two-fold crystallographic symmetry axis along the binding channel, a statistical disorder model must be applied, giving rise to two ligand binding modes in each of the two binding sites of tetrameric TTR. Water molecules were added based upon the unbiased electron density map. Because of the lack of interpretable electron densities in the final map, the nine N-terminal and three C-terminal residues were not included in the final model.

Since modifications would be apparent to those of skill in the art, the subject matter claimed herein is intended to be limited only by the scope of the appended claims.

What is claimed is:

1. A compound having the formula:

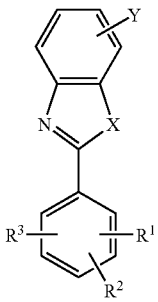

or pharmaceutically acceptable salts, esters, enol ethers, enol esters, acetals, ketals, orthoesters, hemiacetals, hemiketals, hydrates, or prodrugs thereof, wherein:

Y is tetrazolyl, CONHOH, $B(OH)_2$, $CONHSO_2Ar$, $CONHCH(R^6)COOH$, or $-(CH_2)_n-C(R^6)(NH_2)-COOH$;

X is O;

$R^1$, $R^2$ and $R^3$ are each independently selected from halo and OH;

Ar is aryl, optionally substituted with halo, OR, alkyl or haloalkyl;

R is hydrogen, alkyl, alkenyl, alkynyl, cycloalkyl, heterocyclyl, aryl or heteroaryl;

$R^6$ is the side chain of a naturally occurring α-amino carboxylic acid; and n is an integer from 0-3.

2. A compound having the formula:

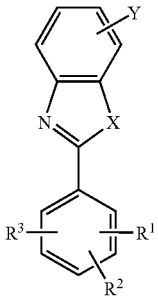

or pharmaceutically acceptable salts, esters, enol ethers, enol esters, acetals, ketals, orthoesters, hemiacetals, hemiketals, hydrates, or prodrugs thereof, wherein:

Y is tetrazolyl, CONHOH, $B(OH)_2$, $CONHSO_2Ar$, $CONHCH(R^6)COOH$, or $-(CH_2)_n-C(R^6)(NH_2)-COOH$;

X is O;

$R^1$, $R^2$ and $R^3$ are each independently selected from halo and $B(OH)_2$;

Ar is aryl, optionally substituted with halo, OR, alkyl or haloalkyl;

R is hydrogen, alkyl, alkenyl, alkynyl, cycloalkyl, heterocyclyl, aryl or heteroaryl;

$R^6$ is the side chain of a naturally occurring α-amino carboxylic acid; and n is an integer from 0-3.

3. The compound of claim 1, wherein $R^1$ and $R^2$ are each halo and $R^3$ is OH.

4. The compound of claim 2, wherein $R^1$ and $R^2$ are each halo and $R^3$ is $B(OH)_2$.

5. A pharmaceutical composition, comprising a compound of claim 1 or claim 2 and a pharmaceutically acceptable carrier.

6. The pharmaceutical composition of claim 5 formulated for single dosage administration.

7. A method for the stabilization of transthyretin in a tissue or in a biological fluid, comprising administration of a compound of claim 1 or claim 2.

8. A method of inhibiting transthyretin misfolding, comprising contacting the transthyretin with a compound of claim 1 or claim 2.

9. A method of treating, or ameliorating one or more symptoms of a transthyretin amyloid disease in a patient, wherein the transthyretin amyloid disease is familial amyloid polyneuropathy, familial amyloid cardiomyopathy, or senile systemic amyloidosis, comprising administering to the patient a compound of claim 1 or claim 2.

10. A method of inhibiting dissociation of a transthyretin tetramer by kinetic stabilization of the native state of the transthyretin tetramer, comprising contacting the tetramer with a compound of claim 1 or claim 2.

11. A method of treating or ameliorating one or more symptoms of a disease in a patient, wherein the disease is selected from Alzheimer's disease, spongiform encephalopathy, polyneuropathy, type II diabetes and medullary carcinoma of the thyroid, comprising administering to the patient a compound of claim 1 or claim 2.

12. A method of treating or ameliorating one or more symptoms of a transthyretin mediated disease or disorder in a patient, wherein the disease is obesity, comprising administering a compound of claim 1 or claim 2 to the patient.

13. A method of stabilizing a transthyretin tetramer, comprising contacting the tetramer with a compound of claim 1 or claim 2.

14. A method of inhibiting formation of TTR amyloid in a patient, comprising administering to the patient a compound of claim 1 or claim 2.

* * * * *